United States Patent
Garruto et al.

(10) Patent No.: US 12,053,547 B2
(45) Date of Patent: Aug. 6, 2024

(54) LIPOSOMAL COMPOSITIONS AND METHODS OF USE

(71) Applicant: Alastin Skincare, Inc., Carlsbad, CA (US)

(72) Inventors: John A. Garruto, Encinitas, CA (US); Alan David Widgerow, Irvine, CA (US)

(73) Assignee: Alastin Skincare, Inc., Carlsbad, CA (US)

( * ) Notice: Subject to any disclaimer, the term of this patent is extended or adjusted under 35 U.S.C. 154(b) by 158 days.

(21) Appl. No.: 17/373,564

(22) Filed: Jul. 12, 2021

(65) Prior Publication Data

US 2021/0338581 A1 Nov. 4, 2021

Related U.S. Application Data

(63) Continuation of application No. 16/529,577, filed on Aug. 1, 2019, now Pat. No. 11,103,455.

(60) Provisional application No. 62/713,995, filed on Aug. 2, 2018, provisional application No. 62/714,007, filed on Aug. 2, 2018.

(51) Int. Cl.
| | |
|---|---|
| *A61K 9/127* | (2006.01) |
| *A61K 38/05* | (2006.01) |
| *A61K 38/06* | (2006.01) |
| *A61K 38/08* | (2019.01) |
| *A61P 3/04* | (2006.01) |

(52) U.S. Cl.
CPC ............ *A61K 9/127* (2013.01); *A61K 9/1278* (2013.01); *A61K 38/05* (2013.01); *A61K 38/06* (2013.01); *A61K 38/08* (2013.01); *A61P 3/04* (2018.01)

(58) Field of Classification Search
None
See application file for complete search history.

(56) References Cited

U.S. PATENT DOCUMENTS

| | | |
|---|---|---|
| 3,299,037 A | 1/1967 | Boissonnas et al. |
| 3,415,805 A | 12/1968 | Siedel et al. |
| 5,534,420 A | 7/1996 | Debono et al. |
| 5,814,610 A | 9/1998 | Bab et al. |
| 5,993,787 A | 11/1999 | Sun et al. |
| 6,939,854 B2 | 9/2005 | Priestley |
| 6,974,799 B2 | 12/2005 | Lintner |
| 7,361,634 B2 | 4/2008 | Trotter et al. |
| 7,544,375 B1 | 6/2009 | Bellin et al. |
| 7,566,464 B2 | 7/2009 | Belfer |
| 7,632,527 B2 | 12/2009 | Jochim et al. |
| 7,750,115 B2 | 7/2010 | Oka et al. |
| 7,772,196 B2 | 8/2010 | Yedgar |
| 7,943,156 B2 | 5/2011 | Alminana et al. |
| 8,021,695 B2 | 9/2011 | Gruber |
| 8,025,907 B2 | 9/2011 | Belfer |
| 8,067,370 B2 | 11/2011 | Trotter et al. |
| 8,071,139 B2 | 12/2011 | Widgerow |
| 8,076,312 B2 | 12/2011 | Yedgar |
| 8,183,204 B2 | 5/2012 | Pickart |
| 8,304,393 B2 | 11/2012 | Oka et al. |
| 8,394,371 B2 | 3/2013 | Laurent-Applegate et al. |
| 8,449,879 B2 | 5/2013 | Laurent-Applegate et al. |
| 8,529,925 B2 | 9/2013 | Alexiades-Armenakas |
| 8,530,426 B2 | 9/2013 | Lintner et al. |
| 8,575,106 B2 | 11/2013 | Santhanam et al. |
| 8,591,961 B2 | 11/2013 | Widgerow |
| 8,697,656 B2 | 4/2014 | Fournial et al. |
| 8,710,010 B2 | 4/2014 | Van et al. |
| 8,710,011 B2 | 4/2014 | Garcia Sanz et al. |
| 8,796,315 B2 | 8/2014 | Mccord |
| 8,815,266 B2 | 8/2014 | Carreño et al. |
| 8,901,103 B2 | 12/2014 | Yedgar |
| 8,906,426 B2 | 12/2014 | Galderisi |
| 8,916,539 B2 | 12/2014 | Yedgar et al. |
| 8,946,166 B2 | 2/2015 | Garcia et al. |
| 8,962,565 B2 | 2/2015 | Dal et al. |
| 8,993,716 B2 | 3/2015 | Carreno et al. |
| 9,000,033 B2 | 4/2015 | Gruber |
| 9,067,967 B2 | 6/2015 | García et al. |
| 9,078,903 B2 | 7/2015 | Laurent-Applegate et al. |
| 9,144,434 B1 | 9/2015 | Rodan et al. |
| 9,180,157 B2 | 11/2015 | Widgerow |
| 9,180,158 B2 | 11/2015 | Widgerow |
| 9,248,160 B1 | 2/2016 | Obagi et al. |
| 9,265,792 B2 | 2/2016 | Riley |
| 9,266,921 B2 | 2/2016 | Garcia et al. |
| 9,278,122 B2 | 3/2016 | Laurent-Applegate et al. |
| 9,315,564 B2 | 4/2016 | Serraima et al. |
| 9,333,152 B2 | 5/2016 | Ferrer et al. |
| 9,364,414 B2 | 6/2016 | Domloge et al. |
| 9,376,659 B2 | 6/2016 | Rao et al. |
| 9,408,881 B2 | 8/2016 | Gruber et al. |
| 9,434,764 B2 | 9/2016 | Abdel-Malek et al. |

(Continued)

FOREIGN PATENT DOCUMENTS

| | | |
|---|---|---|
| CA | 2768653 A1 | 3/2011 |
| CA | 2895387 A1 | 7/2014 |

(Continued)

OTHER PUBLICATIONS

Active Concepts. AC Dermal Respiratory Factor Advanced PF. Technical Data Sheet. (4 pgs.) (2014).

(Continued)

*Primary Examiner* — Nannette Holloman

(74) *Attorney, Agent, or Firm* — Sunit Talapatra; Foley & Lardner LLP

(57) ABSTRACT

Provided herein are liposomal compositions for improved delivery and penetration into the skin. Liposomal compositions as provided herein comprise one more peptides. Also provided herein are compositions and methods for targeting dermal white adipose tissue to improve fat reduction and anti-aging effects. Compositions and methods for targeting dermal white adipose tissue may comprise administering a composition comprising liposomes.

13 Claims, 12 Drawing Sheets
(5 of 12 Drawing Sheet(s) Filed in Color)

(56) References Cited

U.S. PATENT DOCUMENTS

| | | |
|---|---|---|
| 9,486,409 B2 | 11/2016 | Edelson et al. |
| 9,526,679 B2 | 12/2016 | Jang et al. |
| 9,725,483 B2 | 8/2017 | Garcia et al. |
| 9,834,580 B2 | 12/2017 | Abdel-Malek et al. |
| 10,086,035 B2 | 10/2018 | Garruto et al. |
| 10,286,030 B2 | 5/2019 | Garruto et al. |
| 10,493,011 B2 | 12/2019 | Widgerow et al. |
| 10,688,147 B2 | 6/2020 | Garruto et al. |
| 11,103,455 B2 | 8/2021 | Garruto et al. |
| 2003/0166571 A1 | 9/2003 | Judd |
| 2003/0223938 A1 | 12/2003 | Nagy et al. |
| 2004/0043047 A1 | 3/2004 | Dumas et al. |
| 2004/0120918 A1 | 6/2004 | Lintner et al. |
| 2005/0063932 A1 | 3/2005 | Dilallo et al. |
| 2006/0110355 A1 | 5/2006 | Blin |
| 2006/0198800 A1 | 9/2006 | Dilallo et al. |
| 2007/0048245 A1 | 3/2007 | Belfer |
| 2007/0110731 A1 | 5/2007 | Riley |
| 2008/0044373 A1 | 2/2008 | Ilekti et al. |
| 2008/0107679 A1 | 5/2008 | Dilallo et al. |
| 2008/0152606 A1 | 6/2008 | Reinhart et al. |
| 2008/0166313 A1 | 7/2008 | Jochim et al. |
| 2008/0166314 A1 | 7/2008 | Jochim et al. |
| 2008/0171011 A1 | 7/2008 | Jochim et al. |
| 2008/0171030 A1 | 7/2008 | Jochim et al. |
| 2008/0171031 A1 | 7/2008 | Jochim et al. |
| 2008/0175928 A1 | 7/2008 | Jochim et al. |
| 2008/0181974 A1 | 7/2008 | Cauchard et al. |
| 2008/0213300 A1 | 9/2008 | Jochim et al. |
| 2009/0047226 A1 | 2/2009 | Teckenbrock et al. |
| 2009/0186826 A1 | 7/2009 | Lintner et al. |
| 2009/0285770 A1 | 11/2009 | Laboureau |
| 2010/0021401 A1 | 1/2010 | Sallander |
| 2010/0047296 A1 | 2/2010 | Banowski et al. |
| 2010/0183723 A1 | 7/2010 | Laurent-Applegate et al. |
| 2010/0189795 A1 | 7/2010 | Dreher |
| 2010/0316745 A1 | 12/2010 | Pellicier et al. |
| 2010/0322983 A1 | 12/2010 | Griffiths-Brophy et al. |
| 2011/0005737 A1 | 1/2011 | Plata |
| 2011/0020242 A1 | 1/2011 | Zheng et al. |
| 2011/0052676 A1 | 3/2011 | Gruber |
| 2011/0059907 A1 | 3/2011 | Gupta et al. |
| 2011/0091420 A1 | 4/2011 | Liu et al. |
| 2011/0158922 A1 | 6/2011 | Dupont et al. |
| 2011/0177140 A1 | 7/2011 | Voegeli et al. |
| 2012/0021029 A1 | 1/2012 | Garcia et al. |
| 2012/0045405 A1 | 2/2012 | Gilman et al. |
| 2012/0076842 A1 | 3/2012 | Fournial et al. |
| 2012/0128755 A1 | 5/2012 | Gruber et al. |
| 2012/0277313 A1 | 11/2012 | Kwon et al. |
| 2013/0129691 A1 | 5/2013 | Laurent-Applegate et al. |
| 2013/0224131 A1 | 8/2013 | Voegeli et al. |
| 2013/0337088 A1 | 12/2013 | Widgerow |
| 2014/0127286 A1 | 5/2014 | Doucet et al. |
| 2014/0178315 A1 | 6/2014 | Gruber et al. |
| 2014/0242134 A1 | 8/2014 | Khoshdel et al. |
| 2014/0309173 A1 | 10/2014 | Dreher |
| 2014/0315995 A1 | 10/2014 | Dreher et al. |
| 2014/0364819 A1 | 12/2014 | Vandelden |
| 2015/0050331 A1 | 2/2015 | Needleman |
| 2015/0057244 A1 | 2/2015 | Yedgar et al. |
| 2015/0157728 A1 | 6/2015 | Modi |
| 2015/0183823 A1 | 7/2015 | García et al. |
| 2015/0202139 A1 | 7/2015 | Friedman |
| 2015/0209282 A1 | 7/2015 | Chu et al. |
| 2015/0342852 A1 | 12/2015 | Van et al. |
| 2015/0342854 A1 | 12/2015 | Shibuya et al. |
| 2016/0000858 A1 | 1/2016 | Tittl et al. |
| 2016/0006543 A1 | 1/2016 | Winstead et al. |
| 2016/0008263 A1 | 1/2016 | Mendoza |
| 2016/0030321 A1 | 2/2016 | Dreher |
| 2016/0058693 A1 | 3/2016 | Widgerow |
| 2016/0058816 A1 | 3/2016 | Widgerow |
| 2016/0075738 A1 | 3/2016 | Ferrer et al. |
| 2016/0243023 A1* | 8/2016 | Sente .................. A61K 8/9711 |
| 2017/0001438 A1 | 1/2017 | Seto et al. |
| 2017/0081508 A1 | 3/2017 | Daniere et al. |
| 2017/0101438 A1 | 4/2017 | García et al. |
| 2017/0135930 A1 | 5/2017 | Korth |
| 2017/0157014 A1 | 6/2017 | Peschard et al. |
| 2017/0202769 A1 | 7/2017 | Pilant |
| 2017/0281507 A1 | 10/2017 | Idkowiak-Baldys et al. |
| 2017/0281508 A1 | 10/2017 | Idkowiak-Baldys et al. |
| 2017/0304178 A1 | 10/2017 | Idkowiak-Baldys et al. |
| 2018/0066016 A1 | 3/2018 | Abdel-Malek et al. |
| 2020/0338154 A1 | 10/2020 | Garruto et al. |
| 2021/0030640 A1* | 2/2021 | Kim .................. A61K 8/63 |
| 2021/0205405 A1 | 7/2021 | Garruto et al. |

FOREIGN PATENT DOCUMENTS

| | | |
|---|---|---|
| CN | 103505377 A | 1/2014 |
| CN | 104069043 A | 10/2014 |
| CN | 104523449 A | 4/2015 |
| CN | 104523554 A | 4/2015 |
| CN | 104586695 A | 5/2015 |
| CN | 104622779 A | 5/2015 |
| CN | 103601792 B | 6/2016 |
| CN | 107375041 A | 11/2017 |
| DE | 102004050563 A1 | 4/2006 |
| DE | 102004055541 A1 | 5/2006 |
| DE | 102004057405 A1 | 6/2006 |
| DE | 102004057406 A1 | 6/2006 |
| DE | 102005063179 A1 | 9/2006 |
| DE | 102006046076 A1 | 4/2007 |
| DE | 102005056157 A1 | 5/2007 |
| DE | 102005063062 A1 | 7/2007 |
| DE | 102005063178 A1 | 7/2007 |
| DE | 102006004955 A1 | 7/2007 |
| DE | 102006020380 A1 | 10/2007 |
| DE | 102006040903 A1 | 3/2008 |
| DE | 102006041291 A1 | 3/2008 |
| DE | 102007022448 A1 | 3/2008 |
| DE | 102007024381 A1 | 3/2008 |
| DE | 102006049672 A1 | 4/2008 |
| DE | 102006049674 A1 | 4/2008 |
| DE | 102006049675 A1 | 4/2008 |
| DE | 102007022449 A1 | 4/2008 |
| DE | 102006058611 A1 | 6/2008 |
| DE | 102006060439 A1 | 6/2008 |
| DE | 102006061829 A1 | 6/2008 |
| DE | 102006062438 A1 | 7/2008 |
| DE | 102006062501 A1 | 7/2008 |
| DE | 102006062566 A1 | 7/2008 |
| DE | 102007024384 A1 | 11/2008 |
| DE | 102007031452 A1 | 1/2009 |
| DE | 102008028821 A1 | 1/2009 |
| DE | 102008061045 A1 | 10/2009 |
| DE | 102008032179 A1 | 1/2010 |
| DE | 102009026718 A1 | 4/2010 |
| DE | 102008053883 A1 | 5/2010 |
| DE | 102008053884 A1 | 5/2010 |
| DE | 102008059703 A1 | 6/2010 |
| DE | 102008061044 A1 | 6/2010 |
| DE | 102008062398 A1 | 6/2010 |
| DE | 102009037537 A1 | 6/2010 |
| DE | 102009037900 A1 | 6/2010 |
| DE | 102009039393 A1 | 6/2010 |
| DE | 102009045981 A1 | 8/2010 |
| DE | 102008061340 A1 | 9/2010 |
| DE | 102009002226 A1 | 10/2010 |
| DE | 102009002227 A1 | 10/2010 |
| DE | 102009002287 A1 | 10/2010 |
| DE | 102009017612 A1 | 10/2010 |
| DE | 102009026414 A1 | 11/2010 |
| DE | 102009027024 A1 | 12/2010 |
| DE | 102009029813 A1 | 12/2010 |
| DE | 102010027180 A1 | 5/2011 |
| DE | 102010028418 A1 | 11/2011 |
| DE | 102010063585 A1 | 6/2012 |
| DE | 102011084904 A1 | 6/2012 |
| DE | 102011087999 A1 | 9/2012 |
| DE | 102012222967 A1 | 9/2013 |
| DE | 102012222764 A1 | 10/2013 |

(56) References Cited

FOREIGN PATENT DOCUMENTS

| | | |
|---|---|---|
| EP | 2266529 A2 | 12/2010 |
| EP | 2514403 A1 | 10/2012 |
| EP | 2740484 A1 | 6/2014 |
| EP | 2792684 A1 | 10/2014 |
| FR | 2668365 A1 | 4/1992 |
| JP | 2011246372 A | 12/2011 |
| RU | 2591789 C1 | 7/2016 |
| WO | WO-9910374 A1 | 3/1999 |
| WO | WO-2005016364 A1 | 2/2005 |
| WO | WO-2005048968 A1 | 6/2005 |
| WO | WO-2006131234 A1 | 12/2006 |
| WO | WO-2007000214 A1 | 1/2007 |
| WO | WO-2007017196 A2 | 2/2007 |
| WO | WO-2007059822 A1 | 5/2007 |
| WO | WO-2007078056 A1 | 7/2007 |
| WO | WO-2008003685 A1 | 1/2008 |
| WO | WO-2008058943 A2 | 5/2008 |
| WO | WO-2008065072 A1 | 6/2008 |
| WO | WO-2008090226 A2 | 7/2008 |
| WO | WO-2008151257 A2 | 12/2008 |
| WO | WO-2008155382 A2 | 12/2008 |
| WO | WO-2008155391 A2 | 12/2008 |
| WO | WO-2009026949 A1 | 3/2009 |
| WO | WO-2009059205 A1 | 5/2009 |
| WO | WO-2009114959 A1 | 9/2009 |
| WO | WO-2010019939 A1 | 2/2010 |
| WO | WO-2010037553 A1 | 4/2010 |
| WO | WO-2010049011 A2 | 5/2010 |
| WO | WO-2010049389 A1 | 5/2010 |
| WO | WO-2010049390 A1 | 5/2010 |
| WO | WO-2010049457 A2 | 5/2010 |
| WO | WO-2010118880 A1 | 10/2010 |
| WO | WO-2011028673 A2 | 3/2011 |
| WO | WO-2012010684 A2 | 1/2012 |
| WO | WO-2012010685 A2 | 1/2012 |
| WO | WO-2012044745 A2 | 4/2012 |
| WO | WO-2012098116 A1 | 7/2012 |
| WO | WO-2012130775 A1 | 10/2012 |
| WO | WO-2012143845 A2 | 10/2012 |
| WO | WO-2012164488 A2 | 12/2012 |
| WO | WO-2013060707 A2 | 5/2013 |
| WO | WO-2013075017 A1 | 5/2013 |
| WO | WO-2013091975 A1 | 6/2013 |
| WO | WO-2013092080 A1 | 6/2013 |
| WO | WO-2014081845 A2 | 5/2014 |
| WO | WO-2014090524 A2 | 6/2014 |
| WO | WO-2014110613 A1 | 7/2014 |
| WO | WO-2014120793 A1 | 8/2014 |
| WO | WO-2014140890 A2 | 9/2014 |
| WO | WO-2016007314 A1 | 1/2016 |
| WO | WO-2016046848 A2 | 3/2016 |
| WO | WO-2016097966 A1 | 6/2016 |
| WO | WO-2017001625 A1 | 1/2017 |
| WO | WO-2017136600 A1 | 8/2017 |
| WO | WO-2017216177 A1 | 12/2017 |
| WO | WO-2019028275 A1 | 2/2019 |

OTHER PUBLICATIONS

Alkemade et al. SKALP/elafin is an inducible proteinase inhibitor in human epidermal keratinocytes. Journal of Cell Science 107:2335-2342 (1994).
Al-Rimawi et al. Formulation and evaluation of a moisturizing day cream containing olive leaves extract. Int J Devel Res 4(10):1996-2000 (2014).
Ashcroft et al. Age-Related Changes in the Temporal and Spatial Distributions of Fibrillin and Elastin Mrnas and Proteins in Acute Cutaneous Wounds of Healthy Humans. Journal of Pathology 183:80-89 (1997).
Bani et al. Histological and Ultrastructural Effects of Ultrasound-induced Cavitation on Human Skin Adipose Tissue. Plast Reconstr Surg Glob Open 1(6):e41 (2013).
Bauters et al. Gelatinase A (MMP2) promotes marine adipogenesis. Biochimica et Biophysica Acta (BBA) General Subjects 1850:1449-1456 (2015).
Bekker et al. Relating rheological measurements to primary and secondary skin feeling when mineral-based and Fischer-Tropsch wax-based cosmetic emulsions and jellies are applied to the skin. Int J Cosmet Sci 35(4):354-361 (2013).
'BioBustyl: A genuine firmness and tone concentrate for the bust' Sederma Brochure (7 pgs.) (Feb. 2008).
Bitto et al. Long-term IGF-I exposure decreases autophagy and cell viability. PLOS One 5(9): e12592 (2010).
Blanchevoye et al. Interaction between the Elastin Peptide VGVAPG and Human Elastin Binding Protein. J Biol Chem 288:1317-1328 (2012).
Brandner et al. Caffeine improves barrier function in male skin. International Journal of Cosmetic Science 28:343-347 (2006).
Brazilian Patent Application No. BR112018015897-6 Office Action dated Apr. 29, 2021.
Bylka et al. Centella asiatica in cosmetology. Postepy Dermatol Alergol 30(1):46-49 (2013).
Canadian Patent Application No. 3,013,459 Office Action dated Dec. 9, 2019.
Cappellano et al. Dermal white adipose tissue renewal is regulated by the PDGFA/AKT axis. Stem Cell Investig 4:23 (2017).
Carruthers et al. Cryolipolysis and skin tightening. Dermatol Surg 40(Suppl. 12):S184-S189 (2014).
CASAS. 2019 ASAPS—Examination of healing and recovery outcomes post cosmetic surgery and non-surgical body contouring procedures with a novel topical body treatment incorporating Tripeptide and Hexapeptide (TriHex) technology. Abstract 2019.
CELLDETOX® Product brochure. Silab (3 pgs.) (2013).
Cenizo et al. LOXL as a target to increase the elastin content in adult skin: a dill extract induces the LOXL gene expression. Experimental Dermatology 15:574-581 (2006).
Chiang et al. Current concepts related to hypertrophic scarring in burn injuries. Wound Repair Regen 24(3):466-77 (2016).
Cho et al. Phosphatidylserine prevents UV-induced decrease of type I procollagen and increase of MMP-1 in dermal fibroblasts and human skin in vivo. J Lipid Res 49(6):1235-1245 (2008).
Cianfanelli et al. Ambra1 at a glance. J Cell Sci 128(11):2003-8 (2015).
Codogno et al. Atg5: more than an autophagy factor. Nature Cell Biology 8(10):1045-1048 (2006).
De Backer et al. Controlling MicroRNAs to Fight Skin Senescence. Cosmetics & Toiletries Available at https://www.cosmeticsandtoiletries.com/research/biology/Controlling-MicroRNAs-to-Fight-Skin-Senescen . . . (Feb. 4, 2016) (6 pgs.).
Donati et al. Epidermal Wnt/β-catenin signaling regulates adipocyte differentiation via secretion of adipogenic factors. PNAS USA 111(15):E1501-E1509. (2014).
Dow Corning 9040 Silicone Elastomer Blend product Information (7 pgs) (Apr. 3, 2012).
Draelos et al. Glycation and Skin Aging: A Review. Cosmetics & Toiletries Magazine (3 pgs.) (Jun. 2011).
Driskell et al. Defining dermal adipose tissue. Exp Dermatol 23(9):629-631 (2014).
Duncan et al. A prospective study analyzing the application of radiofrequency energy and high-voltage, ultrashort pulse duration electrical fields on the quantitative reduction of adipose tissue. J Cosmet Laser Ther 18(5):257-67 (2016).
Emami-Razavi et al. Effect of Bentonite on Skin Wound Healing: Experimental Study in the Rat Model. Acta Medica Iranica 44(4):235-240 (2006).
ESSENSKIN™ The essential by instinct. Brochure (2 pgs.) (2008).
European Application No. 17748189.2 International Search Report and Written Opinion dated Jul. 25, 2019.
European Application No. 17748189.2 Office Action dated Mar. 15, 2021.
European Patent Application No. 18842077.2 Extended Supplemental European Search Report dated Jun. 16, 2021.
EWC's Skin Deep Cosmetics Database 'System JO Maximizer Shaping Cream' Nov. 2014 Retrieved from the internet: <URL: http:www.ewg.orgskindeepproduct526533System_JO_Maximizer_Shaping_Cream> (5 pgs).

(56) References Cited

OTHER PUBLICATIONS

EWG's Skin Deep Cosmetics Database: System JO Maximizer Shaping Cream; XP009512694; Washington (2014).
Fligiel et al. Collagen degradation in aged/photodamaged skin in vivo and after exposure to matrix metalloproteinase-1 in vitro. J Invest Dermatol 120:842-848 (2003).
Floquet et al. Structural Characterization of VGVAPG an Elastin-Derived Peptide. Biolpolymers 76:266-280 (2004).
Foster et al., Dermal white adipose tissue undergoes major morphological changes during the spontaneous and induced murine hair follicle cycling: a reappraisal. Archives of Dermatological Research 310(5):453-462. doi: 10.1007/s00403-018-1831-y (2018).
Garibyan et al. Three-dimensional volumetric quantification of fat loss following cryolipolysis. Lasers Surg Med 46(2):75-80 (2014).
Gautam, et al. Topical Delivery of Protein and Peptide Using Novel Cell Penetrating Peptide IMT-P8. Sci. Rep. 6, 26278 (2016).
Grant et al. Fat in flames: influence of cytokines and pattern recognition receptors on adipocyte lipolysis. Am J Physiol Endocrinol Metab 309(3):E205-13 (2015).
Gregory et al. The macrophage and the apoptotic cell: an innate immune interaction viewed simplistically? Immunology 113:1-14 (2004).
Gruber et al. Modulation of cellular senescence in fibroblasts and dermal papillae cells in vitro. J Cosmet Sci. 64(2):79-87 (2013) (Abstract).
Hakozaki et al. The effect of niacinamide on reducing cutaneous pigmentation and suppression of melanosome transfer. Br J Dermatol 147:20-31 (2002).
He et al. Receptor for advanced glycation end products binds to phosphatidylserine and assists in the clearance of apoptotic cells. EMBO Reports 12(4):358-364 (2011).
Hocker et al. Inhibition of autophagy through MAPK14-mediated phosphorylation of ATG5. Autophagy 9(3):426-428 (2013).
Ingargiola et al. Cryolipolysis for fat reduction and body contouring: safety and efficacy of current treatment paradigms. Plast Reconstr Surg 135(6):1581-90 (2015).
International Application No. PCT/US2019/044714 Invitation to Pay Additional Fees dated Oct. 1, 2019.
Ito et al. Is the Hair Follicle Necessary for Norm Wound Healing. J Invest Dermatol 128:1059-1061 (2008).
Jain et al.: Transfollicular drug delivery: current perspectives. Research and Reports in Transdermal Drug Delivery. (2016).
Jalian et al. Paradoxical adipose hyperplasia after cryolipolysis. JAMA Dermatol 150(3):317-9 (2014).
Japanese Patent Application No. 2018-539307 Office Action dated Sep. 30, 2020.
Johnson et al. Controlled delivery of heparin-binding EGF-like growth factor yields fast and comprehensive wound healing. J Control Release 166(2):124-129 (2013).
Johnson et al.: Safety Assessment of Tripeptide-1, Hexapeptide-12, their Metal Salts and Fatty Acyl Derivatives, and Palmitoyl Tetrapeptide-7 as Used in Cosmetics. Cosmetic Ingredient Review. 37(Supplement 3):90S-102S (2014) https:www.cir-safety.org/sites/default/files/tripep062014final.pdf.
Jose et al. Enhanced trophic factor secretion by mesenchymal stem/stromal cells with Glycine-Histidine-Lysine (GHK)-modified alginate hydrogels. Acta Biomater 10(5):1955-1964 (2014).
Katsiki et al. The olive constituent oleuropein exhibits proteasome stimulatory properties in vitro and confers life span extension of human embryonic fibroblasts. Rejuvenation Res 10(2):157-172 (2007).
Khamlue et al. Skin Wound Healing Promoting Effect of Polysaccharides Extracts from Tremella fuciformis and Auricularia auricula on the ex-vivo Porcine Skin Wound Healing Model. 2012 4th International Conference on Chemical, Biological and Environmental Engineering IPCBEE 43:93-98 (2012).
Kilmer et al. Safety and efficacy of cryolipolysis for non-invasive reduction of submental fat. Lasers Surg Med 48(1):3-13 (2016).
Kontogianni et al. Olive leaf extracts are a natural source of advanced glycation end product inhibitors. J Med Food 16(9):817-822 (2013).
Koo et al. Protection from photodamage by topical application of caffeine after ultraviolet irradiation. Br J Dermatol 156(5):957-964 (2007).
Kovac et al. *Plantago lanceolata* L. water extract induces transition of fibroblasts into myofibroblasts and increases tensile strength of healing skin wounds. J Pharm Pharmacol 67(1):117-125 (2015).
Kruglikov et al. Skin aging: are adipocytes the next target? Aging (Albany NY) 8(7):1457-1469 (2016).
Laatikainen et al. SOD3 decreases ischemic injury derived apoptosis through phosphorylation of Erk1/2, Akt, and FoxO3a. PLoS One 6(8):e24456 (2011).
Lee et al. Protective effect and mechanism of phosphatidylserine in UVB-induced human dermal fibroblasts. Eu J Lipid Sci Technol 115(7):783-790 (2013).
Li et al. Antioxidant and anti-inflammatory activities of methanol extracts of Tremella fuciformis and its major phenolic acids. J Food Sci 79(4):C460-468 (2014).
Liao et al. Antioxidative activity, moisture retention, film formation, and viscosity stability of *Auricularia fuscosuccinea*, white strain water extract. Biosci Biotechnol Biochem 78(6):1029-1036 (2014).
Liu et al. Elastic fiber homeostasis requires lysyl oxidase-like 1 protein.Nat Genet. 36(2):178-182 (2004).
Luebberding et al. Age-related changes in skin barrier function—quantitative evaluation of 150 female subjects.Int J Cosmet Sci. 35(2):183-190 (2013).
Lupo et al. Cosmeceutical peptides. Dermatol Ther 20:343-349 (2007).
Mahmoudi et al. Comparing the effects of Bentonite & Calendula on the improvement of infantile diaper dermatitis: A randomized controlled trial. Indian J Med Res 42:742-746 (2015).
Maixner et al. Autophagy in Adipose Tissue. Obes Facts. 5(5):710-721 (2012).
Manstein et al. Selective cryolysis: A novel method of non-invasive fat removal. Lasers in Surgery and Medicine 40(9):595-604 (2008).
Marigliano et al.: Use of peptides in anti-aging functional cosmetology. Household and Personal Care Today. Tekno Scienze. Milano, IT. 4(1):4-11 (2010).
Marino et al. Human autophagins, a family of cysteine proteinases potentially implicated in cell degradation by autophagy. J Biol Chem 278(6):3671-8 (2003).
Mohan et al.: Encapsulation of bioactive whey peptides in soy lecithin-derived nanoliposomes: Influence of peptide molecular weight. ScienceDirect. Food Chemistry 213:143-148 (2016).
Nagase Chemtex PIPS; Phosphatidylserine & phosphatidylinositol (4 pgs) (May 2015).
Navarrete-Solis et al. A Double-Blind, Randomized Clinical Trial of Niacinamide 4% versus Hydroquinone 4% in the Treatment of Melasma. Dermatol Res Pract 2011:379173 (2011).
NIOD Lip Bio Lipid Concentrate. British Beauty Blogger (2015).
Noblesse et al. Lysyl oxidase-like and lysyl oxidase are present in the dermis and epidermis of a skin equivalent and in human skin and are associated to elastic fibers. J Invest Dermatol 122(3):621-630 (2004).
Ojima et al. Dynamics of protein secretion during adipocyte differentiation. FEBS Open Bio 6(8):816-26 (2016).
Omar. Oleuropein in olive and its pharmacologic effects. Sci Pharm 78(2):133-154 (2010).
Park et al. High-Intensity Focused Ultrasound for the Treatment of Wrinkles and Skin Laxity in Seven Different Facial Areas. Ann Dermatol 27(6):688-693 (2015).
PCT/US2017/016292 International Search Report and Written Opinion dated May 12, 2017.
PCT/US2018/045045 International Preliminary Report on Patentability dated Feb. 4, 2020.
PCT/US2018/045045 International Search Report and Written Opinion dated Oct. 10, 2018.
PCT/US2019/044714 International Search Report and Written Opinion dated Dec. 3, 2019.
PCT/US2019/044714 PCT Communication dated Sep. 28, 2020.

(56) References Cited

OTHER PUBLICATIONS

Pereira et al. The role of inflammation in adipocytolytic nonsurgical esthetic procedures for body contouring. Clinical, Cosmetic and Investigational Dermatology 10:57-66 (2017).
PHYTOSONIC™ Brochure. Sederma (2 pgs.) (Sep. 2008).
Pickart et al.: GHK Peptide as a Natural Modulator of Multiple Cellular Pathways in Skin Regeneration. Hindawi Publishing Corp. BioMed Research International. Article ID 648108, 7 pages (2015).
Pickart et al. The Human Tripeptide GHKCU in Prevention of Oxidative Stress and Degenerative Conditions of Aging: Implications for Cognitive Health. Oxid Med Cell Longev 2012:324832 (2012).
Pickart. The human tri-peptide GHK and tissue remodeling. J Biomater Sci Polym Ed 19:969-988 (2008).
Plikus et al. Regeneration of fat cells from myofibroblasts during wound healing. Science 355(6326):748-752 (2017).
Preissig et al. Current laser resurfacing technologies: A review that delves beneath the surface. Semin Plast Surg 26(3):109-116 (2012).
PRO-LIPO ™ NEO. Smart Lipsome Preparation. LucasMeyer Cosmetics PowerPoint Presentation (25 pgs) (viewed Aug. 2018).
Remington: The science and practice of pharmacy. 20th Edition. Gennaro, Eds. Lippincott Williams & Wilkins, 2003.
Remington. The Science and Practice of Pharmacy. Mack Publishing Company, 19th Edition, 1995.
Resh. Fatty acylation of proteins: new insights into membrane targeting of myristoylated and palmitoylated proteins. Biochimica et Biophysica Acta 1451:1-16 (1999).
Rigacci et al. Oleuropein aglycone induces autophagy via the AMPK/mTOR signalling pathway: a mechanistic insight. Oncotarget 6(3):35344-35357 (2015).
Rivera-Gonzalez et al. Skin Adipocyte Stem Cell Self-Renewal is Regulated by a PDGFA/AKT-Signaling Axis. Cell Stem Cell 19(6):738-751 (2016).
Rnjak et al. Severe Burn Injuries and the Role of Elastin in the Design of Dermal Substitutes. Tissue Eng Part B Rev 17(2):81-91 (2011).
Russell et al. Studies on the antiobesity effect of zinc-alpha2-glycoprotein in the ob/ob mouse. Int J Obes (Lond) 35(3):345-354 (2011).
Seaman et al. Paradoxical Adipose Hyperplasia and Cellular Effects After Cryolipolysis: A Case Report. Aesthet Surg J 36(1):NP6-13 (2016).
Senior et al. Val-Gly-Val-Ala-Pro-Gly, a repeating peptide in elastin, is chemotactic for fibroblasts and monocytes. J Cell Biol 99:870-874 (1984).
Shadfar et al. Anatomy and Physiology of the Aging Neck. Facial Plast Surg Clin North Am. 22(2):161-170 (2014).
Shirakata et al. Heparin-binding EGF-like growth factor accelerates keratinocyte migration and skin wound healing. J Cell Sci 118(Pt 11):2363-2370 (2005).
Simeon et al. Expression and activation of matrix metalloproteinases in wounds: modulation by the tripeptide-copper complex glycyl-L-histidyl-L-lysine-Cu2+. J Invest Dermatol 112:957-962 (1999).
Simons. Angiogenesis: where do we stand now? Circulation 111(12):1556-1566 (2005).
Sinambela et al., Human in vivo study: dermal application of Rutin SmartCrystals ® & peptide-loaded liposomes to decrease skin roughness. 40th Annual Meeting of the Controlled Release Society (2013).
Singh et al. Lipophagy: Connecting Autophagy and Lipid Metabolism. Int J Cell Biol. 2012:282041 (2012).
Skaltsounisd et al. Redox Biol. Aug. 2015;5:20515. doi: 10.1016j.redox.2015.04.010 (13 pgs.) (Epub Apr. 29, 2015).
Sklirou et al. Hexapeptide-11 is a novel modulator of the proteostasis network in human diploid fibroblasts. Redox Biology 5:205-215 (2015).
SymDecanox HA. New Generation of Antioxidant. Symris Brochure (34 pgs) (2015).
Takeuchi et al. Inhibition of platelet-derived growth factor signalling induces autophagy in malignant glioma cells. Br J Cancer 90(5):1069-75 (2004).
Tsai et al. How irritant is water? An overview. Contact Dermatitis 41(6):311-314 (1999).
Unisooth PN47. Induchem Switzerland. (15 pgs) (Sep. 21, 2010).
Uplevity™. Lipotec. Technical Report (25 pgs) (Jun. 2013).
U.S. Appl. No. 15/423,530 1st Action Interview dated Sep. 6, 2017.
U.S. Appl. No. 15/423,530 Office Action dated Dec. 18, 2017.
U.S. Appl. No. 15/423,530 PreInterview Action dated May 25, 2017.
U.S. Appl. No. 16/004,259 Office Action dated Sep. 26, 2018.
U.S. Appl. No. 16/053,674 Preinterview Office Action dated Jan. 25, 2019.
U.S. Appl. No. 16/529,577 Office Action dated Sep. 3, 2020.
U.S. Appl. No. 16/570,732 Office Action dated Nov. 16, 2020.
U.S. Appl. No. 16/870,643 Final Office Action dated Aug. 11, 2021.
U.S. Appl. No. 16/870,643 Office Action dated Apr. 9, 2021.
U.S. Appl. No. 17/192,494 Office Action dated May 14, 2021.
U.S. Appl. No. 17/192,494 Office Action dated Sep. 3, 2021.
Van Zutphen et al. Lipid autophagy in the yeast *Saccharomyces cerevisiae*. Mol Biol Cell 25(2):290-301 (2014).
Verma et al. Transfollicular drug delivery: current perspectives. Research and Reports in Transdermal Drug Delivery 5:1-17 (2016).
Verma. Particle size of liposomes influences dermal delivery of substances into skin. International Journal of Pharmaceutics 258(1-2):141-151 (2003).
Vilchez et al. Marine carotenoids: biological functions and commercial applications. Mar Drugs 9(3):319-333 (2011).
Vogt et al. 40 nm, but not 750 or 1,500 nm, nanoparticles enter epidermal CD1a+ cells after transcutaneous application on human skin. J Invest Dermatol 126(6):1316-22 (2006).
Vural et al. Autophagy in macrophages: impacting inflammation and bacterial infection. Scientifica (Cairo) 2014:825463 (2014).
Wang. Lipid droplets, lipophagy, and beyond. Biochim Biophys Acta 1861(8 Pt B):793-805 (2016).
Wen et al. Xylose phosphorylation functions as a molecular switch to regulate proteoglycan biosynthesis. PNAS USA 111(44):15723-15728 (2014).
Widgerow. Chronic wound fluid-thinking outside the box. Wound Repair Regen 19(3):287-291 (2011).
Widgerow et al. A Double-Blind Randomized controlled Trial Evaluation the Efficacy and Tolerability of a Topical body Treatment in Combination With Cryolipolysis Procedures. J Drugs Dermatol 18(4):342-348 (2019).
Widgerow et al. Extracellular Matrix Modulation: Optimizing Skin Care and Rejuvenation Procedures. J Drugs Dermatol 15(4s):S63-S71 (2016).
Widgerow et al. Non-Surgical Fat Reduction and Topical Modulation of Adipose Tissue Physiology. J Drugs Dermatol 18(4):375-380 (2019).
Widgerow et al. Preoperative Skin Conditioning: Extracellular Matrix Clearance and Skin Bed Preparation, A New Paradigm. Aesthetic Surgery Journal39(S3):S103-S111 (2019).
Widgerow. Topical Skin Restoration Technology—Advances in Age Management Strategies. Modern Aesthetics (8 pgs.) (May/Jun. 2016).
Wohlrab et al. Niacinamide—Mechanisms of Action and its Topical Use in Dermatology. Skin Pharmacol Physiol 27:311-315 (2014).
Wu et al. Caspases: a molecular switch node in the crosstalk between autophagy and apoptosis. Int J Biol Sci 10(9):1072-83 (2014).
Zhang et al. Induction of autophagy is essential for monocyte-macrophage differentiation. Blood 119(12):2895-2905 (2012).
Zoumalan. Topical Agents for Scar management: Are They Effective? J Drugs Dermatol 17(4):421-425 (Apr. 2018).

\* cited by examiner

LIPOSOMAL COMPOSITIONS AND METHODS OF USE

CROSS-REFERENCE

This application is a continuation of U.S. application Ser. No. 16/529,577 filed on Aug. 1, 2019, which claims the benefit of U.S. Provisional Patent Application No. 62/713,995 filed on Aug. 2, 2018 and U.S. Provisional Patent Application No. 62/714,007 filed on Aug. 2, 2018, each of which is incorporated herein by reference in its entirety.

BACKGROUND

Many methods and compositions exist for delivering therapeutics to treat a disorder or disease. However, such methods and compositions are not entirely efficacious.

Several non-surgical and surgical fat removal procedures are increasingly used to reduce fat. Non-surgical fat removal procedures include technology that uses heat or cooling or an injected medication to reduce fat cells. However, these procedures may not be the most effective at reducing fat

BRIEF SUMMARY

Efficacy of an active ingredient depends on several factors including its bioavailability. For topical compositions, skin penetration ability is important for bioavailability of the active ingredient. Some methods for improving skin penetration and bioavailability can be too aggressive such as methods employing a skin barrier disrupter like an alcohol. Delivery systems employing liposomes may improve delivery and skin penetration in a safe and efficacious manner.

Described herein are liposomal compositions for improved distribution, efficacy, bioavailability, and/or activity. Liposomal compositions may improve distribution, efficacy, bioavailability, and/or activity by improving delivery and skin penetration.

An aspect described herein is a composition comprising a non-palmitoylated peptide encapsulated in a liposome, wherein an average particle size of the composition is no more than 220 nanometers. In one feature, the peptide comprises an acetyl peptide. In one feature, the peptide is a hexapeptide. In one feature, the hexapeptide is hexapeptide-11. In one feature, the hexapeptide is hexapeptide-38. In one feature, the hexapeptide-38 comprises acetyl hexapeptide-38. In one feature, the average particle size is about 150 nanometers to about 220 nanometers. In one feature, the average particle size is about 180 nanometers to about 220 nanometers. In one feature, the average particle size is about 185 nanometers. In one feature, the average particle size is about 180 nanometers. In one feature, a polydispersity index is about 0.17. In one feature, the composition comprises about 0.03% of the peptide. In one feature, the composition comprises about 0.01% to about 5% of the peptide. In one feature, the composition comprises at most about 5% of the peptide. In one feature, the composition comprises about 27% of liposomes. In one feature, the composition comprises about 20% to about 40% of liposomes. In one feature, the composition comprises about 10% to about 30% of liposomes. In one feature, the composition is oil free. In one feature, the composition is preservative free. In one feature, the composition comprises a pH in a range of about 5 to about 8. In one feature, the composition comprises about 1.5×, 2.0×, 2.5×, 3.0×, or 4.0× improved efficacy as compared to a composition not comprising liposomes. In one feature, the composition comprises about 1.5×, 2.0×, 2.5×, 3.0×, or 4.0× improved distribution as compared to a composition not comprising liposomes. In one feature, the composition comprises about 1.5×, 2.0×, 2.5×, 3.0×, or 4.0× increased activity as compared to a composition not comprising liposomes. In one feature, the composition is a topical composition. In one feature, the composition further comprises hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof. In one feature, the composition further comprises a tripeptide, a tetrapeptide, and a second hexapeptide. In one feature, the tripeptide is tripeptide-1. In one feature, the tripeptide-1 comprises palmitoyl tripeptide-1, myristoyl tripeptide-1, or a combination thereof. In one feature, the tetrapeptide is tetrapeptide-2. In one feature, the tetrapeptide-2 comprises acetyl tetrapeptide-2. In one feature, the second hexapeptide is hexapeptide-12. In one feature, the hexapeptide-12 comprises palmitoyl hexapeptide-12, myristoyl hexapeptide-12, or a combination thereof. In one feature, the composition further comprises water, glycerin, propanediol, niacinamide, isopropyl palmitate, polyacrylate-13, phosphatidylserine, ascorbyl palmitate, *Swertia chirata* extract, hydrolyzed pea protein, ornithine, ceramide NP, ergothioneine, *Dunaliella salina* extract, phytosterols, phospholipids, glycolipids, *Tremella fuciformis* sporocarp extract, *Olea europaea* (olive) fruit oil, *Butyrospermum parkii* (shea) butter, betaine, squalane, lecithin, caprylyl methicone, disodium EDTA, polysorbate 20, tocopherol, butylene glycol, caprylyl glycol, caprylhydroxamic acid, polyisobutene, ethylhexylglycerin, phenoxyethanol, or combinations thereof. In one feature, the composition further comprises a tripeptide, a dipeptide, and a second hexapeptide. In one feature, the tripeptide is tripeptide-1. In one feature, the tripeptide-1 comprises palmitoyl tripeptide-1, myristoyl tripeptide-1, or a combination thereof. In one feature, the tripeptide is tripeptide-5. In one feature, the tripeptide-5 comprises palmitoyl tripeptide-5, myristoyl tripeptide-5, or a combination thereof. In one feature, the second hexapeptide is hexapeptide-12. In one feature, the hexapeptide-12 comprises palmitoyl hexapeptide-12, myristoyl hexapeptide-12, or a combination thereof. In one feature, the dipeptide is dipeptide-5. In one feature, the liposome comprises phospholipids. In one feature, the liposome comprises phospholipids, fatty acids, or fatty acid groups. In one feature, the phospholipids are unsaturated. In one feature, the phospholipids have a transition phase temperature from about 10° C. to about 25° C.

An aspect described herein is a composition comprising a peptide encapsulated in a liposome, wherein an average particle size of the composition is no more than 220 nanometers, and wherein the peptide is not functionalized or is functionalized with a functional group comprising no more than fourteen carbons. In one feature, the peptide comprises an acetyl peptide. In one feature, the peptide is a hexapeptide. In one feature, the hexapeptide is hexapeptide-11. In one feature, the hexapeptide is hexapeptide-38. In one feature, the hexapeptide-38 comprises acetyl hexapeptide-38. In one feature, the average particle size is about 150 nanometers to about 220 nanometers. In one feature, the average particle size is about 180 nanometers to about 220 nanometers. In one feature, the average particle size is about 185 nanometers. In one feature, the average particle size is about 180 nanometers. In one feature, a polydispersity index is about 0.17. In one feature, the composition comprises about 0.03% of the peptide. In one feature, the composition comprises about 0.01% to about 5% of the peptide. In one feature, the composition comprises at most about 5% of the peptide. In one feature, the composition comprises about 27% of liposomes. In one feature, the composition comprises about 20% to about 40% of liposomes. In one feature, the composition comprises about 10% to about 30% of liposomes. In one feature, the composition is oil free. In one feature, the composition is preservative free. In one feature, the composition comprises a pH in a range of about 5 to about 8. In one feature, the composition comprises about 1.5×, 2.0×, 2.5×, 3.0×, or 4.0× improved efficacy as compared to a composition not comprising liposomes. In one feature, the composition comprises about 1.5×, 2.0×, 2.5×, 3.0×, or 4.0× improved distribution as compared to a composition not comprising liposomes. In one feature, the composition comprises about 1.5×, 2.0×, 2.5×, 3.0×, or 4.0× increased activity as compared to a composition not comprising liposomes. In one feature, the composition is a topical composition. In one feature, a composition further comprises hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof. In one feature, a composition further comprises a tripeptide, a tetrapeptide, and a second hexapeptide. In one feature, the tripeptide is tripeptide-1. In one feature, the tripeptide-1 comprises palmitoyl tripeptide-1, myristoyl tripeptide-1, or a combination thereof. In one feature, the tetrapeptide is tetrapeptide-2. In one feature, the tetrapeptide-2 comprises acetyl tetrapeptide-2. In one feature, the second hexapeptide is hexapeptide-12. In one feature, the hexapeptide-12 comprises palmitoyl hexapeptide-12, myristoyl hexapeptide-12, or a combination thereof. In one feature, a composition further comprises water, glycerin, propanediol, niacinamide, isopropyl palmitate, polyacrylate-13, phosphatidylserine, ascorbyl palmitate, *Swertia chirata* extract, hydrolyzed pea protein, ornithine, ceramide NP, ergothioneine, *Dunaliella salina* extract, phytosterols, phospholipids, glycolipids, *Tremella fuciformis* sporocarp extract, *Olea europaea* (olive) fruit oil, *Butyrospermum parkii* (shea) butter, betaine, squalane, lecithin, caprylyl methicone, disodium EDTA, polysorbate 20, tocopherol, butylene glycol, caprylyl glycol, caprylhydroxamic acid, polyisobutene, ethylhexylglycerin, phenoxyethanol, or combinations thereof. In one feature, a composition further comprises a tripeptide, a dipeptide, and a second hexapeptide. In one feature, the tripeptide is tripeptide-1. In one feature, the tripeptide-1 comprises palmitoyl tripeptide-1, myristoyl tripeptide-1, or a combination thereof. In one feature, the tripeptide is tripeptide-5. In one feature, the tripeptide-5 comprises palmitoyl tripeptide-5, myristoyl tripeptide-5, or a combination thereof. In one feature, the second hexapeptide is hexapeptide-12. In one feature, the hexapeptide-12 comprises palmitoyl hexapeptide-12, myristoyl hexapeptide-12, or a combination thereof. In one feature, the dipeptide is dipeptide-5. In one feature, the liposome comprises phospholipids. In one feature, the liposome comprises phospholipids, fatty acids, or fatty acid groups. In one feature, the phospholipids are unsaturated. In one feature, the phospholipids have a transition phase temperature from about 10° C. to about 25° C.

An aspect described herein is a method for preparing a composition comprising a peptide encapsulated in a liposome, comprising: (a) combining the peptide and a solvent to form a mixture; and (b) contacting the mixture with an aqueous solution comprising liposomes; wherein an average particle size of the composition is no more than 220 nanometers. In one feature, the contacting occurs at a temperature between about 10° C. to about 25° C. In one feature, the contacting occurs at a temperature between about 21° C. to about 25° C. In one feature, the peptide comprises an acetyl peptide. In one feature, the peptide is a hexapeptide. In one feature, the hexapeptide is hexapeptide-11. In one feature, the hexapeptide is hexapeptide-38. In one feature, the hexapeptide-38 comprises acetyl hexapeptide-38. In one feature, the solvent is butylene glycol. In one feature, the solvent is propanediol. In one feature, the solvent is water. In one feature, the average particle size is about 150 nanometers to about 220 nanometers. In one feature, the average particle size is about 180 nanometers to about 220 nanometers. In one feature, the average particle size is about 185 nanometers. In one feature, the average particle size is about 180 nanometers. In one feature, a polydispersity index is about 0.17. In one feature, the composition comprises about 0.03% of the peptide. In one feature, the composition comprises about 0.01% to about 5% of the peptide. In one feature, the composition comprises at most about 5% of the peptide. In one feature, the composition comprises about 27% of liposomes. In one feature, the composition comprises about 20% to about 40% of liposomes. In one feature, the composition comprises about 10% to about 30% of liposomes. In one feature, the composition is oil free. In one feature, the composition is preservative free. In one feature, the composition comprises a pH in a range of about 5 to about 8. In one feature, the composition comprises about 1.5×, 2.0×, 2.5×, 3.0×, or 4.0× improved efficacy as compared to a composition not comprising liposomes. In one feature, the composition comprises about 1.5×, 2.0×, 2.5×, 3.0×, or 4.0× improved distribution as compared to a composition not comprising liposomes. In one feature, the composition comprises about 1.5×, 2.0×, 2.5×, 3.0×, or 4.0× increased activity as compared to a composition not comprising liposomes. In one feature, the composition is a topical composition. In one feature, the aqueous solution comprises about 50%, 60%, 70%, 80%, or 90% water. In one feature, the aqueous solution comprises a ratio of about 1:9 to about 3:7 liposomes to water. In one feature, the liposome comprises phospholipids. In one feature, the liposome comprises phospholipids, fatty acids, or fatty acid groups. In one feature, the phospholipids are unsaturated. In one feature, the phospholipids have a transition phase temperature from about 10° C. to about 25° C. In one feature, an average entrapment efficacy is no more than 100%.

Described herein are methods and compositions for fat reduction and anti-aging. In some instances, methods and compositions as described herein target the fat tissue. In some instances, targeting the dermal white adipose tissue results in improved fat reduction. In some instances, targeting the dermal white adipose tissue results in improved lipid droplet absorption. Methods and compositions as described herein comprise targeting dermal white adipose tissue (dWAT). In some instances, targeting of dWAT may be improved by administration of a composition comprising a peptide encapsulated in a liposome.

An aspect described herein is a method for targeting dermal white adipose tissue (dWAT) comprising: administering a composition through a hair follicle, wherein the composition penetrates the hair follicle to the dWAT. In one feature, the composition comprises a peptide encapsulated in a liposome. In one feature, the peptide is a hexapeptide. In one feature, the hexapeptide is hexapeptide-11. In one feature, an average particle size of the composition is no more than 220 nanometers. In one feature, an average particle size of the composition is about 150 nanometers to about 220 nanometers. In one feature, an average particle size of the composition is about 180 nanometers to about 220 nanometers. In one feature, an average particle size of the composition is about 185 nanometers. In one feature, an average particle size of the composition is about 180 nanometers. In one feature, an active ingredient of the composition is no more than about 600 Daltons. In one feature, an active ingredient of the composition is no more than about 700, 800, 900, or 1000 Daltons. In one feature, the composition comprises about 1.5×, 2.0×, 2.5×, 3.0×, or 4.0× improved efficacy as compared to a composition not comprising liposomes. In one feature, the composition comprises about 1.5×, 2.0×, 2.5×, 3.0×, or 4.0× improved distribution as compared to a composition not comprising liposomes. In one feature, the composition comprises about 1.5×, 2.0×, 2.5×, 3.0×, or 4.0× increased activity as compared to a composition not comprising liposomes. In one feature, the composition is administered following a non-invasive fat reduction procedure. In one feature, the composition is administered during a non-invasive fat reduction procedure. In one feature, the composition is administered prior to a non-invasive fat reduction procedure. In one feature, the non-invasive fat reduction procedure comprises high frequency focused ultrasound, pulsed focus ultrasound, cryolipolysis, radiofrequency induced electroporation, injectable lipolytic agents, or combinations thereof. In one feature, the composition is administered following a body contouring invasive fat reduction procedure. In one feature, the composition is administered during an invasive fat reduction procedure. In one feature, the composition is administered prior to an invasive fat reduction procedure. In one feature, the invasive fat reduction procedure comprises liposuction, abdominoplasty, breast reduction, or combinations thereof. In one feature, the composition is administered following a body contouring invasive fat reduction procedure and a non-invasive fat reduction procedure. In one feature, a method further comprises hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof. In one feature, a method further comprises a tripeptide, a tetrapeptide, and a second hexapeptide. In one feature, the tripeptide is tripeptide-1. In one feature, the tripeptide-1 comprises palmitoyl tripeptide-1, myristoyl tripeptide-1, or a combination thereof. In one feature, the tetrapeptide is tetrapeptide-2. In one feature, the tetrapeptide-2 comprises acetyl tetrapeptide-2. In one feature, the second hexapeptide is hexapeptide-12. In one feature, the hexapeptide-12 comprises palmitoyl hexapeptide-12, myristoyl hexapeptide-12, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

Figure 1A:
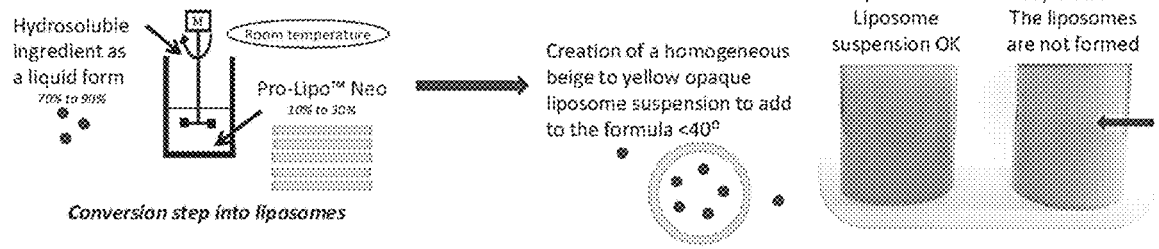
FIGS. 1A-1B show schematics for preparation of liposomes.
Figure 1A:
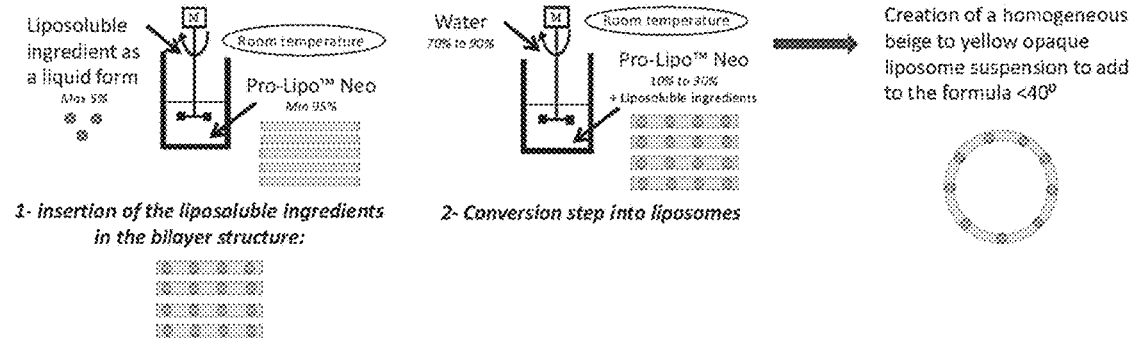
Figure 1A:
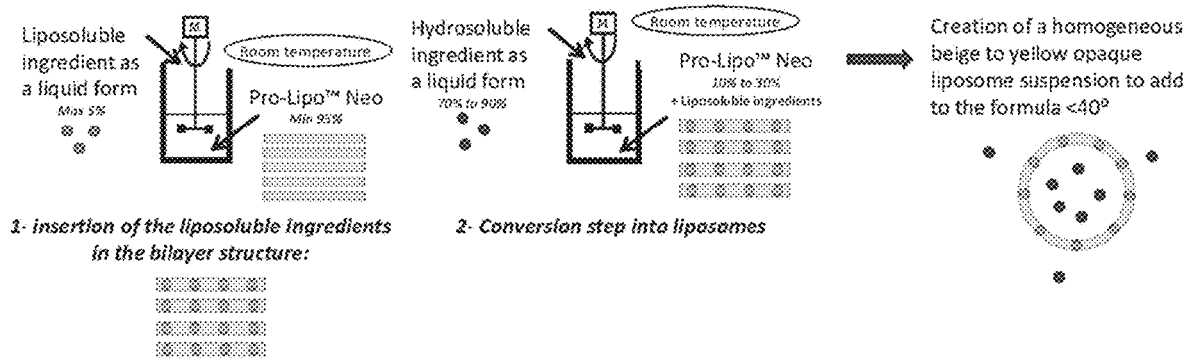

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

Liposomal Compositions

Described herein are liposomal compositions for improved distribution, efficacy, bioavailability, and/or activity. Liposomal compositions may improve distribution, efficacy, bioavailability, and/or activity of the active ingredient by improving delivery and tissue (e.g. skin) penetration. In some instances, improved delivery and skin penetration result from the active ingredient being incorporated (e.g. encapsulated) in a liposome. In some instances, the active ingredient is a peptide that is encapsulated in a liposome.

Described herein are methods for targeting dermal white adipose tissue (dWAT). Targeting dWAT may result in fat reduction and anti-aging effects. In some instances, targeting dWAT comprises administration of a composition with skin penetration ability. In some instances, skin penetration ability is improved by using a composition comprising a peptide incorporated (e.g. encapsulated) in a liposome.

Figure 5:
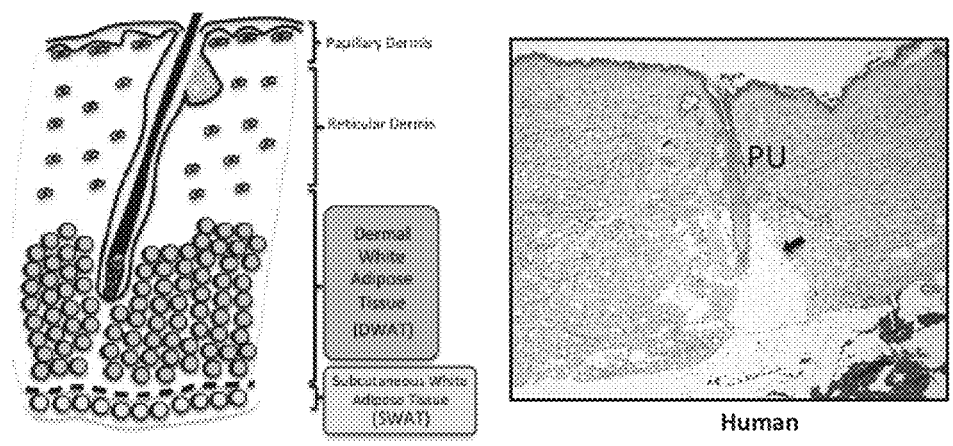
FIG. 5 shows a schematic (left panel) and histological representation (right panel) of dWAT demonstrating direct bridging between dWAT and sWAT compartments.

White adipose tissue (WAT) is no longer considered a simple energy depot and is now recognized as an organ with major endocrine and metabolic effects. Traditionally WAT was considered as two distinct anatomical depots, namely subcutaneous (sWAT) and visceral white adipose tissue (vWAT) with differences in cellular and metabolic effects. Cappellano, G. and C. Ploner, Dermal white adipose tissue renewal is regulated by the PDGFA/AKT axis. Stem Cell Investig, 2017. 4: p. 23. More recently a new type of WAT, dermal WAT (dWAT), has been identified and is recognized as playing a major role in skin processes such as hair follicle growth, thermoregulation, wound healing and signal transmission. Cappellano, G. and C. Ploner, Dermal white adipose tissue renewal is regulated by the PDGFA/AKT axis. Stem Cell Investig, 2017. 4: p. 23. This layer lies in the reticular dermis encasing mature hair follicles (FIG. 5). Driskell, R. R., et al., Defining dermal adipose tissue. Exp Dermatol, 2014. 23(9): p. 629-31. In addition this fat compartment is associated with specific adipose stem cell phenotypes (CD24+), distinctly different to sWAT, suggesting unique functions of this fat depot. Cappellano, G. and C. Ploner, Dermal white adipose tissue renewal is regulated by the PDGFA/AKT axis. Stem Cell Investig, 2017. 4: p. 23. dWAT is organized in cone-like structures (often identified in deeper skin graft donor areas) and are particularly associated with scarring when exposed at that depth. Chiang, R. S., et al., Current concepts related to hypertrophic scarring in burn injuries. Wound Repair Regen, 2016. 24(3): p. 466-77 and Kruglikov, I. and P. E. Scherer, Skin aging: are adipocytes the next target? AGING, 2016. 8(7): p. 1457-1470.

dWAT may also communicate to sWAT to form "fat bridges" between these two compartments. Furthermore dWAT can modulate its structure and turnover of adipocytes at far higher rates than sWAT.

Described herein are methods for targeting dermal white adipose tissue (dWAT) comprising administering an active agent through a hair follicle, wherein the active agent is delivered to the dWAT through the hair follicle. In some instances, an active agent of low molecular weight is delivered through the hair follicle through the dWAT. In some instances, the active agent has a molecular weight of no more than about 600 Daltons (Da). In some instances, the active agent has a molecular weight of at least or about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more than 1000 Daltons (Da). In some instances, the active agent has a molecular weight of at least or about 1000, 1100, 1200, 1300, 1400, 1500, 1600, 1700, 1800, 1900, 2000, 2100, 2200, 2300, 2400, 2500, 2600, 2700, 2800, 2900, 3000, 4000, 5000, 6000, or more than 6000 Daltons (Da). In some instances, the active agent has a molecular weight in a range of about 50 to about 1000, about 100 to about 900, about 200 to about 800, about 300 to about 700, or about 400 to about 600 Daltons (Da). Alternatively or in combination, the active agent is a peptide encapsulated in a liposome to improve skin penetration through the hair follicle.

In some embodiments, the composition is a topical composition. In some embodiments, the composition is an aqueous formulation. In some embodiments, the composition is an anhydrous formulation.

Methods as described herein for targeting dermal white adipose tissue, in some embodiments, comprise administering a composition comprising a peptide encapsulated in a liposome. In some embodiments, the peptide is hexapeptide-11.

Liposomal compositions as described herein may comprise a peptide encapsulated in a liposome. In some embodiments, the peptide is hexapeptide-11. In some embodiments, the peptide is hexapeptide-38. In some embodiments, the peptide is functionalized with an acetyl group. For example, the peptide is acetyl hexapeptide-38.

Liposomal compositions as described herein may comprise an active ingredient encapsulated in a liposome. In some embodiments, the ingredient is a non-peptide. In some embodiments, the ingredient is ceramide NP. In some embodiments, the ingredient is niacinamide. In some embodiments, the ingredient is larger than 50 kDa.

Lecithin and other phospholipids may be used to prepare liposomes comprising the peptide compositions as described herein. In some instances, the liposomes comprise phospholipids. In some instances, the liposomes comprise phospholipids, fatty acids, or fatty acid groups. The phospholipids, fatty acids, or fatty acid groups may be saturated. The phospholipids, fatty acids, or fatty acid groups may be unsaturated. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes may deliver the peptide compositions as described herein.

The phospholipids used to prepare the liposomal compositions described herein may comprise a transition phase temperature of about 10° C. to about 25° C. In some instances, the phospholipids comprise a transition phase temperature of about 10° C., 12° C., 14° C., 16° C., 18° C., 20° C., 22° C., 24° C., 26° C., 28° C., 30° C., 32° C., 34° C., 36° C., 38° C., 40° C., or more than 40° C. In some instances, the phospholipids comprise a transition phase temperature in a range of about 10° C. to about 40° C., about 12° C. to about 36° C., about 14° C. to about 32° C., about 16° C. to about 20° C., or about 21° C. to about 25° C.

The liposomal composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Described herein, in some embodiments, are methods for preparing a composition comprising a peptide encapsulated in a liposome, comprising: combining the peptide and a solvent to form a mixture; and contacting the mixture with an aqueous solution comprising liposomes. In some instances, the contacting occurs at a temperature between about 10° C. and about 25° C. In some instances, the contacting occurs at a temperature of about 10° C., 12° C., 14° C., 16° C., 18° C., 20° C., 22° C., 24° C., 26° C., 28° C., 30° C., 32° C., 34° C., 36° C., 38° C., 40° C., or more than 40° C. In some instances, the contacting occurs at a temperature in a range of about 10° C. to about 40° C., about 12° C. to about 36° C., about 14° C. to about 32° C., about 16° C. to about 20° C., or about 21° C. to about 25° C.

Methods for preparing a composition comprising a peptide encapsulated in a liposome may comprise use of a solvent. In some instances, the solvent is water. In some instances, the solvent is an organic solvent. Exemplary organic solvents include, but are not limited to, petroleum ether, cyclohexane, toluene, carbon tetrachloride, dichloromethane, chloroform, diethyl ether, diisopropyl ether, ethyl acetate, butanol, n-propanol, ethanol, methanol, polyethylene glycol, propylene glycol, and pyridine. In some instances, the solvent is a glycol. In some instances, the solvent is butylene glycol. In some instances, the solvent is caprylyl glycol. In some instances, the solvent is propanediol (propylene glycol).

The solvent may be used at various percentages. In some instances, the solvent is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10%. The solvent may be propanediol, butylene glycol, or caprylyl glycol.

Methods as described herein, in some embodiments, comprises combining the peptide and a solvent to form a mixture; and contacting the mixture with an aqueous solution comprising liposomes, wherein the aqueous solution comprises a percentage of water and a percentage of liposomes. In some instances, the aqueous solution comprises at least or about 20%, 30%, 40%, 50%, 60%, 70%, 80%, 90%, or more than 90% water. In some instances, the aqueous solution comprises water in a range of about 10% to about 95%, about 20% to about 90%, about 30% to about 85%, about 40% to about 80%, or about 50% to about 60%. In some instances, the aqueous solution comprises at least or about 20%, 30%, 40%, 50%, 60%, or more than 60% liposomes. In some instances, the aqueous solution comprises liposomes in a range of about 10% to about 80%, about 20% to about 70%, or about 30% to about 60%. A ratio of liposomes to water may be in a range of about 1:9 to about 3:7. In some instances, the ratio of liposomes to water may be at least or about 1:10, 1:9, 1:8, 1:7, 1:6, 1:5, 1:4, 1:3, or 1:2.

Methods for generation of liposomal compositions as described herein may result in an entrapment efficacy of no more than 100%. In some instances, the entrapment efficacy is no more than 50%, 60%, 70%, 80%, 90%, 95%, 99%, or 99.5%.

Described herein are liposomal compositions, wherein the peptide comprises a percentage of the composition. In some embodiments, the peptide is provided at least or about 0.0001%, 0.0005%, 0.00055%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% of the composition. In some embodiments, the peptide is provided at least or about 10%, 11%, 12%, 13%, 14%, 15%, 16%, 17%, 18%, 19%, 20%, 22%, 24%, 26%, 28%, 30% or more than 30% of the composition. In some embodiments, the peptide is provided in a range of about 0.001% to about 6%, about 0.002% to about 4%, about 0.01% to about 5%, or about 0.02% to about 2% by weight. In some embodiments, the peptide is provided at about 0.03% of the composition.

Described herein are liposomal compositions, wherein the liposomes comprise a percentage of the composition. In some embodiments, the liposomes are provided at least or about 10%, 11%, 12%, 13%, 14%, 15%, 16%, 17%, 18%, 19%, 20%, 22%, 24%, 26%, 28%, 30% or more than 30% of the composition. In some embodiments, the liposomes are provided in a range of about 5% to about 90%, about 10% to about 80%, about 20% to about 70%, about 30% to about 60%, about 10% to about 30%, or about 20% to about 40%. In some embodiments, the liposomes are provided at about 30%. In some embodiments, the liposomes are provided at 27%.

Liposomal compositions as described herein, in some embodiments, comprise an average particle size of at most 220 nanometers (nm). In some instances, the average particle size is at most 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 230 nm, 240 nm, 250 nm, 260 nm, 270 nm, 280 nm, 290 nm, 300 nm, 320 nm, 340 nm, 360 nm, 380 nm, or 400 nm. In some instances, the average particle size is about 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 230 nm, 240 nm, 250 nm, 260 nm, 270 nm, 280 nm, 290 nm, 300 nm, 320 nm, 340 nm, 360 nm, 380 nm, or 400 nm. In some instances, the average particle size is in a range of about 50 nm to about 500 nm, about 100 nm to about 400 nm, about 150 nm to about 220 nm, about 180 nm to about 220 nm, or about 190 nm to about 210 nm.

In some instances, the liposomal compositions comprise an active agent that has a molecular weight of no more than about 600 Daltons (Da). In some instances, the active agent has a molecular weight of at least or about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more than 1000 Daltons (Da). In some instances, the active agent has a molecular weight of at least or about 1000, 1100, 1200, 1300, 1400, 1500, 1600, 1700, 1800, 1900, 2000, 2100, 2200, 2300, 2400, 2500, 2600, 2700, 2800, 2900, 3000, 4000, 5000, 6000, or more than 6000 Daltons (Da). In some instances, the active agent has a molecular weight in a range of about 50 to about 1000, about 100 to about 900, about 200 to about 800, about 300 to about 700, or about 400 to about 600 Daltons (Da). In some instances, the active agent is a peptide. In some instances, the active agent is a peptide encapsulated in a liposome.

A polydispersity index (PdI) of a liposomal composition as described herein, in some embodiments, is in a range of 0 to about 0.2. In some instances, the polydispersity index is about 0.01, 0.025, 0.05, 0.1, 0.25, 0.3, 0.35, 0.4, 0.45, 0.5, 0.55, 0.6, 0.65, 0.7, 0.75, or 0.8. In some instances, the polydispersity index is in a range of about 0.01 to about 0.8, about 0.025 to about 0.75, about 0.05 to about 0.6, or about 0.1 to about 0.3.

In some instances, an intercept of a liposomal composition as described herein is in a range of about 0.85 to about 0.95. In some instances, the intercept is the amplitude. In some instances, the intercept is at least or about 0.65, 0.70, 0.75, 0.80, 0.85, 0.90, or 0.95.

In some embodiments, the liposomes comprise propanediol, lecithin, or a combination thereof. In some embodiments, the propanediol is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the propanediol is provided in a range of about 0.001% to about 6%, about 0.002% to about 4%, about 0.01% to about 3%, or about 0.02% to about 2% by weight. In some embodiments, the lecithin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the lecithin is provided in a range of about 0.001% to about 6%, about 0.002% to about 4%, about 0.01% to about 3%, or about 0.02% to about 2% by weight. In some embodiments, the liposomes comprise propanediol and lecithin. In some embodiments, the propanediol and lecithin are provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the propanediol and lecithin are provided in a range of about 0.001% to about 6%, about 0.002% to about 4%, about 0.01% to about 3%, or about 0.02% to about 2% by weight. In some embodiments, the propanediol and lecithin are provided at about 0.90% by weight.

Described herein are liposomal compositions comprising improved distribution, efficacy, bioavailability, and/or activity. The liposomal compositions may comprise improved distribution, efficacy, bioavailability, and/or activity as compared to compositions not comprising liposomes. Described herein are methods for targeting dWAT with improved distribution, efficacy, bioavailability, and/or activity. Methods for targeting dWAT with improved distribution, efficacy, bioavailability, and/or activity may comprise administering compositions comprising liposomes. The compositions may comprise improved distribution, efficacy, bioavailability, and/or activity as compared to compositions not comprising liposomes. In some instances, the distribution is improved by at least or about 0.5×, 1.0×, 1.5×, 2.0×, 2.5×, 3.0×, 4.0×, 4.5×, 5×, or more than 5× as compared to compositions not comprising liposomes. In some instances, the efficacy is improved by at least or about 0.5×, 1.0×, 1.5×, 2.0×, 2.5×, 3.0×, 4.0×, 4.5×, 5×, or more than 5× as compared to compositions not comprising liposomes. In some instances, the bioavailability is improved by at least or about 0.5×, 1.0×, 1.5×, 2.0×, 2.5×, 3.0×, 4.0×, 4.5×, 5×, or more than 5× as compared to compositions not comprising liposomes. In some instances, the activity is improved by at least or about 0.5×, 1.0×, 1.5×, 2.0×, 2.5×, 3.0×, 4.0×, 4.5×, 5×, or more than 5× as compared to compositions not comprising liposomes. The distribution, efficacy, bioavailability, and/or activity may be improved by at least or about 10%, 15%, 20%, 25%, 30%, 35%, 40%, 45%, 50%, 55%, 60%, 65%, 70%, 75%, 80%, 85%, 90%, or more than 90% as compared to compositions not comprising liposomes.

Liposomal compositions and methods as described herein, in some embodiments, are topical compositions. In some instances, the liposomal compositions are oil free. In some instances, the liposomal compositions are preservative free. In some embodiments, the liposomal formulation is an aqueous formulation. In some embodiments, the liposomal formulation is an anhydrous formulation. In some instances, the liposomal composition comprises a pH in a range of about 5 to about 8. In some instances, the liposomal composition comprises a pH of at least or about 2, 3, 4, 5, 6, 7, 8, 9, or 10.

Methods and compositions as described herein may result in improved follicular penetration. In some instances, the follicular penetration is improved by at least or about 0.5×, 1.0×, 1.5×, 2.0×, 2.5×, 3.0×, 4.0×, 4.5×, 5×, or more than 5×. The follicular penetration may be improved by at least or about 10%, 15%, 20%, 25%, 30%, 35%, 40%, 45%, 50%, 55%, 60%, 65%, 70%, 75%, 80%, 85%, 90%, or more than 90%. In some instances, compositions result in follicular penetration of a depth of at least or about 0.5, 0.75, 1, 1.25, 1.5, 2, 2.5, 3, 3.5, 4, 4.5, 5, 5.5, 6, 7, 8, 9, 10, or more than 10 millimeters.

Penetration Enhancers

Fatty acids and alcohols can be employed to enhance penetration of the peptides, and to provide a silky feel to formulations, e.g., methanoic acid, ethanoic acid, propanoic acid, butanoic acid, isobutyric acid, pentanoic acid, hexanoic acid, heptanoic acid, octanoic acid, nonanoic acid, decanoic acid, myristoleic acid, isovaleric acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, medium chain fatty acids, e.g., C6-12 fatty acids, or the like. Typical amounts when employed in liposomal compositions are from 1% by weight to 4% by weight.

Other Components

Other components can include anti-inflammatory agents, antioxidants, and solubility enhancers. Exemplary anti-irritation agents include, but are not limited to, panthenyl triacetate and naringenin. Panthenyl triacetate and naringenin are natural plant extracts that reduce redness and water loss through the skin. Typical amounts for anti-irritation agents when employed in liposomal compositions are from 1% by weight to 4% by weight.

Exemplary anti-inflammatory agents include, but are not limited to, *Arnica montana* extract. *Arnica montana* extract includes components such as essential oils, fatty acids, thymol, pseudoguaianolide sesquiterpene lactones and flavanone glycosides. It can exhibit an anti-inflammatory effect. Typical amounts for anti-inflammatory agents when employed in liposomal compositions are from 1% by weight to 4% by weight.

Exemplary antioxidant agents include, but are not limited to, *Dunaliella salina* extract. *Dunaliella salina* extract includes components such as beta carotenes. It can exhibit an antioxidant effect. Typical amounts for anti-inflammatory agents when employed in liposomal compositions are from 0.1% by weight to 2% by weight. In some embodiments, *Dunaliella salina* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4%. In some embodiments, *Dunaliella salina* extract is provided at about 0.0027%.

For example, certain components of the formulation tend to be difficult to solubilize in conventional formulations. Phosphatidylserine and oleuropein are known to exhibit solubility issues. In some embodiments, a siloxane polymer, e.g., caprylyl methicone, is used to solubilize phosphatidylserine. In some embodiments, caprylyl methicone is used to solubilize phosphatidylserine in anhydrous formulations. In some embodiments, panthenyl triacetate and naringenin is used to solubilize oleuropein. For topical compositions containing from about 0.05% by weight to about 0.1% by weight phosphatidylserine and/or from about 0.05% by weight to about 0.1% by weight oleuropein, caprylyl methicone in an amount of from about 0.5% by weight to about 1% by weight of caprylyl methicone can solubilize phosphatidylserine in an anhydrous formulation. In some embodiments, phosphatidylserine is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4%. In some embodiments, the phosphatidylserine is provided at about 0.05% by weight. In some embodiments, the phosphatidylserine is provided at about 0.25% by weight. In some embodiments, the phosphatidylserine is provided at about 1% by weight. In some embodiments, the oleuropein is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the oleuropein is provided in a range of about 0.001% to about 6%, about 0.002% to about 4%, about 0.01% to about 3%, about 0.02% to about 2%, or about 0.01% to about 0.05% by weight. In some embodiments, the oleuropein is provided at about 0.010% by weight. In some embodiments, the oleuropein is provided at about 0.020% by weight. In some embodiments, the oleuropein is provided at about 0.050% by weight. In some embodiments, caprylyl methicone is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4%.

In some embodiments, liposomal compositions comprise *Olea europea* (olive) fruit oil. In some embodiments, the *Olea europea* (olive) fruit oil is provided at least or about 0.001%, 0.005%, 0.006%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.).

Bentonite clays can be employed in conjunction with the peptides to provide impart penetration and adsorption properties to the compositions, and can aid in stabilizing emulsions. Other clays, such as hectorite and magnesium aluminum silicate can also be employed. Bentonite or other clays can be modified to yield an organic modified clay compound. Salts (e.g., quaternary ammonium salts) of fatty acids (e.g., hydrogenated fatty acids) can be reacted with hectorite or other clays. As provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by $\Delta n$, where n indicates the lower numbered carbon of each pair of double-bonded carbon atoms. A shorthand notation specifying total # carbons: # double bonds, $\Delta_{double\ bond\ positions}$ can be employed. For example, $20:4\Delta_{5,8,11,14}$ refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-$\Delta$9-octadecenoate) is a monounsaturated fatty acid, linolenate (all-cis-$\Delta$9,12,15-octadecatrienoate) is a polyunsaturated fatty acid. Fatty acids suitable for use can comprise from 5 to 30 carbon atoms, e.g., 5, 6, 7, 8, 9, 10, 11, 12, 13, 14, 15, 16, 17, 18, 19, 20, 21, 22, 23, 24, 25, 26, 27, 28, 29, or 30 carbon atoms. The fatty acid can be fully saturated, or can include as many double bonds as are feasible for the chain length. Fatty acids suitable for functionalizing hectorite or other clays include palmitic acid and stearic acid. Dialkyl quaternary cationic modifiers include dipalmoyldimonium chloride and distearyldimonium chloride. Amidoamine quaternary cationic modifiers include palmitamidopropyltrimonium chloride cetearyl alcohol and palmitamidopropyltrimonium chloride.

In some embodiments, the peptides can be in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulations include, without limitation, monoglycerides, diglycerides, sulfatides, lysolecithin, phospholipids, saponin, bile acids, and the like. The presence of such additional components can influence the physical state, solubility, stability, rate of release, rate of clearance, and penetration of active ingredients.

In some embodiments, the compositions for topical administration comprise the peptide compositions as described herein and a dermatologically acceptable vehicle.

The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or *arachis* oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the peptides into the skin. An alternative to increasing molecular weight (as with silicone gums) or adding filler (as with silicone compounds) is to partially crosslink siloxane polymers and disperse this material in an appropriate silicone carrier fluid. The resulting dimethicone crosspolymers (also known as silicone elastomers in the personal care industry) differ from basic polydimethylsiloxane (PDMS) because of the cross-linking between the linear polymers. These materials can be employed in peptide formulations, and also offer benefits in scar treatment, periwound protection, and enzyme delivery. In skin care applications, the aesthetics of silicone elastomers (including those with functional groups) and their ability to absorb various oils (e.g., with a dimethicone/vinyl dimethicone crosspolymer such as Dow Corning® 9506 Elastomer Powder) are two of the elastomer's desirable properties. Silicone elastomers have a skin feel different from any of the silicone fluids, described as "smooth," "velvety," and "powdery." It can be modified by controlling the amount of liquid phase in the formula, and therefore the degree of swelling. Due to their film-forming properties, dimethicone crosspolymers can be used as delivery systems for active ingredients such as the peptides described herein, or other formulation components such as oil-soluble vitamins and sunscreens. Sunscreens such as octyl methoxycinnamate can be more efficiently delivered from a formulation containing a silicone elastomer, producing a higher sun protection factor (SPF). Silicone elastomer blends can be used to enhance SPF in oil-in-water formulations containing organic sunscreens. For example, in testing conducted regarding SPF, the addition of 4% silicone elastomer blend to a suncare formulation containing organic sunscreens increased the SPF from 5.7 to 18. This property of the silicone elastomer allows the effectiveness of sunscreen agents in a formulation to be maximized while reducing the amount needed to achieve a desired SPF. As a result, formulation costs can be reduced along with potential irritation caused by sunscreen actives. Accordingly, a higher SPF can be achieved with the same amount of UV absorber, resulting in enhanced performance with no added formulation cost. Silicone elastomers can be produced from linear silicone polymers by a variety of crosslinking reactions, e.g., by a hydrosilylation reaction in which a vinyl group reacts with a silicon hydride. The general process involves linear silicone polymers with reactive sites along the polymer chain reacting with a cross-linker. The dimethicone crosspolymer can be produced either as a gel made of a suspension of elastomer particles swollen in a carrier fluid (e.g., a mixture of high molecular weight silicone elastomer in cyclopentasiloxane such as Dow Corning® 9040 Silicone Elastomer Blend), or as a spray-dried powder (a dimethicone/vinyl dimethicone crosspolymer such as Dow Corning® 9506 Elastomer Powder). The gel form having desirable attributes is cyclomethicone, but low viscosity dimethicones and organic fluids can also be used. Examples of dimethicone crosspolymers in the suspension or gel form are high molecular weight silicone elastomer (12%) in decamethylcyclopentasiloxane (e.g., Dow Corning® ST-Elastomer 10) and a mixture of high molecular weight silicone elastomer in cyclopentasiloxane (e.g., Dow Corning® 9040 Silicone Elastomer Blend), which typically have an elastomer content ranging from 10 to 20% by weight.

The pharmaceutical excipients used in the topical preparations of the peptide compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof. An exemplary chelating agent is disodium EDTA. In some embodiments, the disodium EDTA is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.)

Suitable solvents for an aqueous or hydrophilic liposomal composition include water; ethyl alcohol; isopropyl alcohol; mixtures of water and ethyl and/or isopropyl alcohols; glycerin; ethylene, propylene or butylene glycols; DMSO; and mixtures thereof. In some embodiments, glycerin is provided at least or about 1%, 2%, 3%, 4%, 5%, 6%, 7%, 8%, 9%, 10%, 11%, 12%, or more than 12%. In some embodiments, glycerin is provided at least or about 7%. In some embodiments, glycerin is provided in a range of about 1% to about 12%, about 2% to about 11%, or about 3% to about 10%. Suitable solvents for hydrophobic liposomal compositions include mineral oils, vegetable oils, and silicone oils. If desired, the peptide compositions as described herein may be dissolved or dispersed in a hydrophobic oil phase, and the oil phase may then be emulsified in an aqueous phase comprising water, alone or in combination with lower alcohols, glycerin, and/or glycols. It is generally preferred to employ anhydrous compositions, as the presence of water can result in stinging upon administration to skin tissues subject to laser treatment, chemical peel, dermabrasion, or the like. Anhydrous formulations may also act to prevent the development of water-based irritant contact dermatitis in damaged or sensitive skin, which may produce rashes and skin irritation that may retard wound healing and improvement in skin quality. Tsai, T. F., Maibach, H. I. How irritant is water? An overview. Contact Dermatitis 41(6) (1999): 311-314 (describing contact dermatitis caused by water as an irritant). However, in certain embodiments it may be acceptable to provide water based compositions, or to permit a limited amount of water to be present. For example, water may be present, but at amounts below the threshold at which a stinging sensation when applied to damaged skin may result. Osmotic shock or osmotic stress is a sudden change in the solute concentration around a cell, causing a rapid change in the movement of water across its cell membrane. Under conditions of high concentrations of either salts, substrates or any solute in the supernatant, water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis. Certain of the formulations as described herein can be advantageously employed where it is desirable to minimize osmotic shock.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carrageenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the liposomal compositions include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the liposomal compositions. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1,3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in liposomal compositions include anionic, cationic, nonionic, and zwitterionic surfactants. Preferred ionic emulsifiers include phospholipids, such as lecithin and derivatives.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in liposomal compositions include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the formulation. It is generally observed that the anhydrous formulations of the embodiments exhibit satisfactory stability, such that a preservative can be omitted from the formulation.

Suitable chelating agents for use in liposomal compositions include ethylene diamine tetraacetic acid, alkali metal salts thereof alkaline earth metal salts thereof, ammonium salts thereof, and tetraalkyl ammonium salts thereof.

The carrier preferably has a pH of between about 4.0 and 10.0, more preferably between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The peptide compositions of the embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the formulation, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

When the peptide formulations of the embodiments are administered by subcutaneous injection, it is preferably in the form of a pyrogen-free, parenterally acceptable aqueous solution or oleaginous suspension, emulsion or solution. Suspensions can be formulated according to methods well known in the art using suitable dispersing or wetting agents and suspending agents. The preparation of acceptable aqueous or nonaqueous solutions with suitable properties, e.g., pH, isotonicity, stability, and the like, is within the skill in the art. For example, an isotonic vehicle such as 1,3-butanediol, water, isotonic sodium chloride solution, Ringer's solution, dextrose solution, dextrose and sodium chloride solution, lactated Ringer's solution, or other vehicles as are known in the art can be employed, or a fixed oil can be employed conventionally as a solvent or suspending medium, e.g., synthetic mono or diglycerides, fatty acids, or the like. The peptide formulations can also contain stabilizers, preservatives, buffers, antioxidants, or other additives known to those of skill in the art.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include, but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

In certain embodiments, the addition of emollients, emulsion stabilizers, moisturizers, excipients, and other compounds may be modified to enhance the sensory properties of the topical compositions, including but not limited to: skin feel (silkiness, lightness, creaminess, etc.), absorbency (required time at which product loses wet feel and is no longer perceived on skin), consistency, firmness, spreadability (e.g. viscosity, flow onset, shear rates), stickiness, integrity of shape, glossiness, hydrophilicity or hydrophobicity, and others. Preferably, compositions will have high spreadability and low viscosity properties. Compositions with such properties have been demonstrated to have an enhanced "silky" or "light" skin feel rating (see e.g. Bekker, M. Webber, G., Louw, N. Relating rheological measurements to primary and secondary skin feeling when mineral-based and Fischer-Tropsch wax-based cosmetic emulsions and jellies are applied to the skin, International Journal of Cosmetic Science 2013, 35(4), pp. 354-61).

Liposomal compositions as described herein may comprise ceramide NP. In some embodiments, the ceramide NP is provided at least or about 0.00001%, 0.0005%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the ceramide NP is provided in a range of about 0.001% to about 6%, about 0.002% to about 4%, about 0.01% to about 3%, about 0.02% to about 2%, or about 0.50% to about 0.20% by weight. In some embodiments, the ceramide NP is provided at about 0.001% by weight. In some embodiments, the ceramide NP is provided at about 0.05% by weight.

Liposomal compositions as described herein may comprise niacinamide. In some embodiments, niacinamide is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, niacinamide is provided in a range of about 0.25% to about 10%, about 0.5% to about 8%, about 0.75% to about 6%, or about 1% to about 4% by weight. In some embodiments, niacinamide is provided at about 1% by weight. In some embodiments, niacinamide is provided at about 2% by weight. In some embodiments, niacinamide is provided at about 4% by weight.

In some embodiments, liposomal compositions comprise hydrogenated lecithin, C12-16 alcohols, palmitic acid, or combinations thereof. In some embodiments, hydrogenated lecithin is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, hydrogenated lecithin is provided in a range of about 0.25% to about 10%, about 0.5% to about 8%, about 0.75% to about 6%, or about 1% to about 4% by weight. In some embodiments, hydrogenated lecithin is provided with C12-16 alcohols, palmitic acid, or combinations thereof. In some embodiments, C12-16 alcohols are provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, C12-16 alcohols are provided in a range of about 0.25% to about 10%, about 0.5% to about 8%, about 0.75% to about 6%, or about 1% to about 4% by weight. In some embodiments, palmitic acid is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, palmitic acid is provided in a range of about 0.25% to about 10%, about 0.5% to about 8%, about 0.75% to about 6%, or about 1% to about 4% by weight. In some embodiments, hydrogenated lecithin, C12-16 alcohols, and palmitic acid are provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, hydrogenated lecithin, C12-16 alcohols, and palmitic acid are provided in a range of about 0.25% to about 10%, about 0.5% to about 8%, about 0.75% to about 6%, about 1% to about 4%, or about 1% to about 6% by weight. In some embodiments, hydrogenated lecithin, C12-16 alcohols, and palmitic acid are provided at about 4% by weight. In some embodiments, hydrogenated lecithin, C12-16 alcohols, and palmitic acid are provided at about 5% by weight.

In some embodiments, liposomal compositions comprise avocado extra, shea butter, betonite, or combinations thereof. In some embodiments, avocado extract is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, avocado extract is provided in a range of about 0.01% to about 5%, about 0.02% to about 4%, 0.05% to about 3%, or about 0.1% to about 2% by weight. In some embodiments, shea butter is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, shea butter is provided in a range of about 0.01% to about 5%, about 0.02% to about 4%, 0.05% to about 3%, or about 0.1% to about 2% by weight. In some embodiments, bentonite is provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, bentonite is provided in a range of about 0.01% to about 5%, about 0.02% to about 4%, 0.05% to about 3%, or about 0.1% to about 2% by weight. In some embodiments, avocado extract, shea butter, and bentonite are provided at least or about 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, avocado extract, shea butter, and bentonite are provided in a range of about 0.01% to about 5%, about 0.02% to about 4%, 0.05% to about 3%, about 0.1% to about 2%, or about 0.25% to about 2% by weight. In some embodiments, avocado extract, shea butter, and bentonite are provided at about 0.5% by weight. In some embodiments, avocado extract, shea butter, and bentonite are provided at about 1.0% by weight.

In some embodiments, liposomal formulations as described herein comprise phytoene/phytofluene. In some embodiments, the phytoene/phytofluene is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the phytoene/phytofluene is provided in a range of about 0.25% to about 10%, about 0.5% to about 8%, about 0.75% to about 6%, about 1% to about 4%, or about 0.2% to about 1% by weight. In some embodiments, the phytoene/phytofluene is provided at about 0.2% by weight. In some embodiments, the phytoene/phytofluene is provided at about 0.5% by weight. In some embodiments, the phytoene/phytofluene is provided at about 1.0% by weight.

In some embodiments, liposomal compositions as described herein comprise *Centella asiatica*. In some embodiments, the *Centella asiatica* is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the *Centella asiatica* is provided in a range of about 0.25% to about 10%, about 0.5% to about 8%, about 0.75% to about 6%, or about 1% to about 4% by weight. In some embodiments, the *Centella asiatica* is provided at about 1.0% by weight.

In some embodiments, liposomal compositions as described herein comprise hydroxymethoxyphenyl decanone. In some embodiments, the hydroxymethoxyphenyl decanone is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hydroxymethoxyphenyl decanone is provided in a range of about 0.25% to about 10%, about 0.5% to about 8%, about 0.75% to about 6%, about 1% to about 4%, or about 0.5% to about 2% by weight. In some embodiments, the hydroxymethoxyphenyl decanone is provided at about 1.0% by weight.

In some embodiments, liposomal compositions as described herein comprise polyholosides. In some embodiments, the polyholosides are provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the polyholosides are provided in a range of about 0.25% to about 10%, about 0.5% to about 8%, about 0.75% to about 6%, about 1% to about 4%, or about 2.5% to about 10% by weight. In some embodiments, the polyholosides are provided at about 5.0% by weight.

In some embodiments, liposomal compositions as described herein comprise *Plantago lanceolata*. In some embodiments, the *Plantago lanceolata* is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the *Plantago lanceolata* is provided in a range of about 0.25% to about 10%, about 0.5% to about 8%, about 0.75% to about 6%, or about 1% to about 4% by weight. In some embodiments, the *Plantago lanceolata* is provided at about 2.0% by weight.

In some embodiments, liposomal compositions as described herein comprise dill extract. In some embodiments, the dill extract is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the dill extract is provided in a range of about 0.25% to about 10%, about 0.025% to about 4%, about 0.5% to about 8%, about 0.75% to about 6%, or about 1% to about 4% by weight. In some embodiments, the dill extract is provided at about 1.0% by weight.

In some embodiments, liposomal compositions as described herein comprise hydrolyzed *Candida saitoana* extract. In some embodiments, the hydrolyzed *Candida saitoana* extract is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hydrolyzed *Candida saitoana* extract is provided in a range of about 0.25% to about 10%, about 0.5% to about 8%, about 0.75% to about 6%, or about 1% to about 4% by weight. In some embodiments, the hydrolyzed *Candida saitoana* extract is provided at about 3.0% by weight.

In some embodiments, liposomal compositions as described herein comprise *Euglena gracilis* extract, aqua, caffeine, *Glaucium flavum* leaf extract, or combinations thereof. In some embodiments, formulations as described herein comprising *Euglena gracilis* extract, aqua, caffeine, and *Glaucium flavum* leaf extract are provided at least or about 0.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the *Euglena gracilis* extract, aqua, caffeine, and *Glaucium flavum* leaf extract are provided in a range of about 0.001% to about 6%, about 0.002% to about 4%, about 0.01% to about 3%, or about 0.02% to about 2% by weight. In some embodiments, the *Euglena gracilis* extract, aqua, caffeine, and *Glaucium flavum* leaf extract are provided at about 0.20% by weight.

In some embodiments, liposomal compositions as described herein comprise various plant or floral extracts. In some embodiments, formulations as described herein comprise *Tremella fuciformis* extract or *Tremella*. *Tremella fuciformis* extract is derived from an edible mushroom. In some embodiments, *Tremella fuciformis* extract or *Tremella* is provided at least or about 0.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.). In some embodiments, *Tremella fuciformis* extract or *Tremella* is provided at about 0.0125%. In some embodiments, formulations as described herein comprise *Swertia chirata* extract. In some embodiments, *Swertia chirata* extract is provided at least or about 0.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.). In some embodiments, *Swertia chirata* extract is provided at about 0.04%. In some embodiments, formulations as described herein comprise hydrolyzed pea protein. In some embodiments, hydrolyzed pea protein is provided at least or about 0.001%, 0.002%, 0.005%, 0.01%, 0.02%, 0.03%, 0.04%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.). In some embodiments, hydrolyzed pea protein is provided at about 0.002%.

Liposomal compositions as described herein may further comprise isopropyl palmitate, polyacrylate-13, ascorbyl palmitate, ornithine, ergothioneine, phytosterols, phospholipids, glycolipids, betaine, squalane, polysorbate 20, tocopherol, caprylhydroxamic acid, polyisobutene, ethylhexylglycerin, phenoxyethanol, or combinations thereof. In some embodiments, the isopropyl palmitate, polyacrylate-13, ascorbyl palmitate, ornithine, ergothioneine, phytosterols, phospholipids, glycolipids, betaine, squalane, polysorbate 20, tocopherol, caprylhydroxamic acid, polyisobutene, ethylhexylglycerin, phenoxyethanol, or combinations thereof are provided at least or about 0.0001%, 0.0005%, 0.00055%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10%.

Peptides

Described herein are liposomal compositions, wherein the liposomal compositions comprise a peptide encapsulated in a liposome.

In some instances, a peptide is present at about 50 ppm or less to 1000, 5000, 10000, 50000, 100000, 500000 ppm or more, e.g., 100 ppm of the peptide. The topical formulation can contain from 0.01 wt. % or less (e.g., 0.001 wt. %) to 10 wt. % or more, e.g., 0.01 wt. % to 0.02 wt. %, 0.03 wt. %, 0.04 wt. %, 0.05 wt. %, 0.1 wt. %, 1 wt. % to 5 wt. % or 10 wt. % of the first peptide. In some instances, liposomal compositions comprise a plurality of peptides. In some instances, a peptide of the plurality of peptides is present at about 50 ppm or less to 1000, 5000, 10000, 50000, 100000, 500000 ppm or more, e.g., 100 ppm of the peptide, or any other suitable amount. The liposomal compositions may comprise from 0.01 wt. % or less (e.g., 0.001 wt. %) to 10 wt. % or more, e.g., 0.01 wt. % to 0.02 wt. %, 0.03 wt. %, 0.04 wt. %, 0.05 wt. %, 0.1 wt. %, 1 wt. % to 5 wt. % or 20 wt. % of the peptide. The amount of peptide in the base can be adjusted up or down.

Liposomal compositions as described herein, in some embodiments, comprise a plurality of peptides. In some embodiments, each peptide of the plurality of peptides is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, each peptide of the plurality of peptides is provided in a range of about 0.25% to about 10%, about 0.5% to about 8%, about 0.75% to about 6%, or about 1% to about 4% by weight. In some embodiments, each peptide of the plurality of peptides is provided in a range of about 0.001% to about 6%, about 0.002% to about 4%, about 0.01% to about 3%, or about 0.02% to about 2% by weight.

In some embodiments, the peptide is dipeptide-5, tripeptide-1, tripeptide-5, tetrapeptide-2, hexapeptide-12, hexapeptide-11, hexapapetide-38, or combinations thereof. In some embodiments, the liposomal compositions comprise tripeptide-1, tetrapeptide-2, hexapeptide-11, and hexpeptide-12. In some embodiments, the liposomal compositions comprise dipeptide-5, tripeptide-1, tripeptide-5, hexapeptide-12, and hexpeptide-38.

In some embodiments, the dipeptide-5 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the dipeptide-5 is provided in a range of about 0.25% to about 10%, about 0.5% to about 8%, about 0.75% to about 6%, or about 1% to about 4% by weight.

In some embodiments, the tripeptide-1 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the tripeptide-1 is provided in a range of about 0.25% to about 10%, about 0.5% to about 8%, about 0.75% to about 6%, or about 1% to about 4% by weight.

In some embodiments, the tripeptide-5 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the tripeptide-5 is provided in a range of about 0.25% to about 10%, about 0.5% to about 8%, about 0.75% to about 6%, or about 1% to about 4% by weight.

In some embodiments, the tetrapeptide-2 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the tetrapeptide-2 is provided in a range of about 0.25% to about 10%, about 0.5% to about 8%, about 0.75% to about 6%, or about 1% to about 4% by weight.

In some embodiments, the hexapeptide-12 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hexapeptide-12 is provided in a range of about 0.25% to about 10%, about 0.5% to about 8%, about 0.75% to about 6%, or about 1% to about 4% by weight.

In some embodiments, the hexapeptide-11 is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hexapeptide-11 is provided in a range of about 0.25% to about 10%, about 0.5% to about 8%, about 0.75% to about 6%, or about 1% to about 4% by weight. In some embodiments, the hexapeptide-11 is provided in a range of about 0.001% to about 6%, about 0.002% to about 4%, about 0.01% to about 3%, or about 0.02% to about 2%. In some embodiments, the hexapeptide-11 is provided in a range of about 0.005% to about 0.02% by weight.

In some embodiments, the hexapeptide-38 is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt.) In some embodiments, the hexapeptide-38 is provided in a range of about 0.25% to about 10%, about 0.5% to about 8%, about 0.75% to about 6%, or about 1% to about 4% by weight. In some embodiments, the hexapeptide-38 is provided in a range of about 0.001% to about 6%, about 0.002% to about 4%, about 0.01% to about 3%, or about 0.02% to about 2%. In some embodiments, the hexapeptide-38 is provided in a range of about 0.005% to about 0.02% by weight.

In example embodiments, a weight ratio for the first peptide to the second peptide in a topical formulation is 1 part first peptide to 0.2 to 10 parts second peptide, or 1 to 10 parts second peptide, or 1 to 8 parts second peptide, or 1 to 5.5 parts second peptide. The following nomenclature is employed herein to refer to various amino acids: Alanine (also referred to herein as "Ala" or "A"), Arginine (also referred to herein as "Arg" or "R"), Asparagine (also referred to herein as "Asn" or "N"), Aspartic acid (also referred to herein as "Asp" or "D"), Cysteine (also referred to herein as "Cys" or "C"), Glutamic acid (also referred to herein as "Glu" or "E"), Glutamine (also referred to herein as "Gln" or "Q"), Glycine (also referred to herein as "Gly" or "G"), Histidine (also referred to herein as "His" or "H"), Isoleucine (also referred to herein as "Ile" or "I"), Leucine (also referred to herein as "Leu" or "L"), Lysine (also referred to herein as "Lys" or "K"), Methionine (also referred to herein as "Met" or "M"), Phenylalanine (also referred to herein as "Phe" or "F"), Proline (also referred to herein as "Pro" or "P"), Serine (also referred to herein as "Ser" or "S"), Threonine (also referred to herein as "Thr" or "T"), Tryptophan (also referred to herein as "Trp" or "W"), Tyrosine (also referred to herein as "Tyr" or "Y"), Valine (also referred to herein as "Val" or "V").

In some embodiments, the first peptide is a dipeptide. Suitable dipeptides include but are not limited to those having the following sequence of amino acids: KK, KP, CK, KC, KT, DF, NF, VW, YR, or TT. In some embodiments, the dipeptide has the following amino acid sequence: KV. In other embodiments, the first peptide is a tripeptide. Suitable tripeptides include but are not limited to those having the following sequence of amino acids: HGG, RKR, GHK, GKH, GGH, GHG, KFK, or KPK. In some embodiments, the tripeptide has the following amino acid sequence: KVK. In some embodiments, the first peptide is a tetrapeptide. Suitable tetrapeptides include but are not limited to those having the following sequence of amino acids: GQPR, KTFK, AQTR, or RSRK. In some embodiments, the tetrapeptide has the following amino acid sequence: KDVY. In some embodiments, the second peptide is a pentapeptide. Suitable pentapeptides include but are not limited to those having the following sequence of amino acids: KTTKS, YGGFX, or KLAAK. In some embodiments, the second peptide is a hexapeptide. Suitable hexapeptides include but are not limited to those having the following sequence of amino acids: VGVAPG or GKTTKS. In some embodiments, the hexapeptide has the following sequence of amino acids: FVAPFP. In some embodiments, the second peptide is a heptapeptide. Suitable heptapeptides include but are not limited to one having an amino acid sequence RGYYLLE, or Heptapeptide-6 (a pro-sirtuin peptide). The compositions may include two or more peptides, e.g., two dipeptides and one pentapeptide; one tripeptide and one hexapeptide; one dipeptide, one tripeptide, and one heptapeptide, or the like, provided that the composition contains at least one dipeptide, tripeptide, or tetrapeptide and at least one pentapeptide, hexapeptide, or heptapeptide. In some embodiments, the compositions comprise a tripeptide, a tetrapeptide, and a hexapeptide. In some embodiments, a tripeptide is tripeptide-1. In some embodiments, a tetrapeptide is tetrapeptide-2. In some embodiments, a hexapeptide is hexapeptide-12. In some embodiments, a hexapeptide is hexapeptide-11. In some embodiments, the compositions comprise tripeptide-1, tetrapeptide-2, hexapeptide-12, and hexapeptide-11. In some embodiments, the compositions comprise tripeptide-1, tetrapeptide-2, and hexapeptide-12.

The peptide can be functionalized. For example, the peptide can be functionalized with a fatty acid, e.g., myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, or the like. Examples include palmitoyl hexapeptide-12 (Pal-VGVAPG), palmitoyl tripeptide-1 (Pal-GHK), myristoyl hexapeptide-12 (Myr-VGVAPG), and myristoyl tripeptide-1 (Myr-GHK). Palmitoyl or myristoyl functionalization can be desirable in certain embodiments as it exhibits enhanced penetration when compared to other fatty acids. In some embodiments, the peptide is functionalized with a chemical group. For example, the peptide is functionalized with acetyl. Examples include acetyl tetrapeptide-2. In some instances, the peptide is functionalized with a functional group comprising no more than 14 carbons. In some instances, the peptide is functionalized with a functional group comprising no more than 3, 4, 5, 6, 7, 8, 9, 10, 11, 12, 13, 14, 15, 16, 17, 18, 19, 20, or more than 20 carbons. In some instances, the peptide is non-palmitoylated. Without wishing to be limited to a particular theory, incorporation of the peptide in a liposome, in some embodiments, increases the lipophilicity of a peptide that is functionalized or is not functionalized.

Some embodiments of the methods and compositions provided herein include as a first peptide glycine-histidine-lysine (GHK). GHK is a peptide sequence that is rarely found in the class of proteins in general, but is frequently found in extracellular matrix proteins. The small size of GHK permits it to approach membrane receptors far more easily than larger peptides. Further, its unique, copper-binding structure enhances copper transport into and out of cells and promotes wound healing through several different but related pathways. Due to its strong copper binding structure, GHK can be provided in the form of GHK-Cu (copper-bound GHK form).

In liposomal compositions, the tripeptide is typically present in an amount of from about 50 ppm or less to about 100, 200, 300, 400, or 500 ppm or more, e.g., 50 ppm to 150 ppm.

In liposomal compositions, the hexapeptide is typically present in an amount of from about 50 ppm or less to about 100, 200, 300, 400, or 500 ppm or more, e.g., 50 ppm to 150 ppm.

The peptides can advantageously be provided in a base for suitable for combining with other components of a liposomal composition. The base can include one or more components such as a thickener/binding agent (e.g., pentaerythrityl tetraisostearate), an emollient/dispersing agent (e.g., caprylic/capric triglyceride), a solvent (e.g., propylene carbonate), and/or a rheology modifier/antisettling agent (e.g., disteardimonium hectorite).

Stability Testing

Stability testing of the liposomal compositions can be conducted as follows.

High temperature testing is now commonly used as a predictor of long-term stability. High temperature testing can be conducted at 37° C. (98 F) and 45° C. (113° F.). If a product is stored at 45° C. for three months (and exhibits acceptable stability) then it should be stable at room temperature for two years. A good control temperature is 4° C. (39° F.) where most products will exhibit excellent stability. Sometimes, the product is also be subjected to −10° C. (14° F.) for three months.

In some instances, stability of the product is assessed by passing three cycles of temperature testing from −10° C. (14° F.) to 25° C. (77° F.). In such cases, the product is placed at −10° C. for 24 hours and then placed at room temperature (25° C.) for 24 hours. This completes one cycle. An even more rigorous test is a −10° C. to 45° C. five-cycle test. This puts emulsions under a tremendous stress.

The dispersed phase (of an oil-in-water emulsion) has a tendency to separate and rise to the top of the emulsion forming a layer of oil droplets. This phenomenon is called creaming. Creaming is one of the first signs of impending emulsion instability. A test method to predict creaming is centrifugation. Heat the emulsion to 50° C. (122° F.) and centrifuge it for thirty minutes at 3000 rpm. Then inspect the resultant product for signs of creaming.

Both formulas and packaging can be sensitive to the UV radiation. The product is placed in glass and the actual package in a light box that has a broad-spectrum output. Another glass jar completely covered with aluminum foil serves as a control. Discoloration of the product may be observed.

For all the above mentioned tests the color, odor/fragrance, viscosity, pH value, and, if available, particle size uniformity and/or particle agglomeration under the microscope can be observed.

Therapeutic Uses

Liposomal compositions and methods as described herein may be used for improving skin laxity and reducing fat. Methods and compositions as described herein for targeting dermal white adipose tissue (dWAT) may result in fat reduction or anti-aging effects. In some instances, methods as described herein for targeting dWAT comprises administering a composition comprising liposomes. The ability of liposomal compositions to reduce fat may be due to liposomal penetration to the white adipose tissue. In some instances, the liposomal compositions penetrate to the dermal white adipose tissue (dWAT). In some instances, the liposomal compositions penetrate to the subcutaneous white adipose tissue (sWAT). In some instances, the liposomal compositions penetrate the dWAT which then communicates with and acts as a bridge for delivery of the compositions to the subcutaneous adipose tissue. Liposomal penetration to the white adipose tissue may occur through penetration of the hair follicle. Penetration to the white adipose tissue may occur through penetration through the hair follicle.

In some instances, the liposomal compositions are used for restoring skin complex. In some instances, the liposomal compositions are used for skincare treatment, promoting skin regeneration, and promoting enhanced wound healing. In some embodiments, the formulations described herein are used in conjunction with a fat reduction procedure. In some embodiments, the fat reduction procedure is non-invasive. In some instances, the non-invasive fat-reduction procedure is a hot or cold non-invasive fat reduction procedure. Exemplary non-invasive fat reduction procedures include, but are not limited to, low level laser therapy, infrared light, ultrasound, radiofrequency, and cryolipolysis. In some embodiments, the fat reduction procedure comprises an invasive fat reduction procedure. Exemplary invasive fat reduction procedures include, but are not limited to, the invasive fat reduction procedure comprises liposuction, abdominoplasty, breast reduction, or combinations thereof. In some embodiments, the fat reduction procedure comprises an invasive fat reduction procedure and a non-invasive fat reduction procedure.

In some instances, the compositions as described herein are administered to a site for fat reduction. In some instances, the site for fat reduction is a visible protrusion of fat and/or skin from a body region. In some instances, the body region is a submental region, central abdominal region, face, flank, back, chest, arm, leg, buttock, or combination thereof. In some instances, the compositions as described herein are administered to the skin of the submental region, central abdominal region, face, flank, back, chest, arm, leg, buttock, or combination thereof.

In some instances, the liposomal compositions described herein are administered once per day, twice per day, three times per day or more. The liposomal compositions described herein, in some embodiments, are administered daily, every day, every alternate day, five days a week, once a week, every other week, two weeks per month, three weeks per month, once a month, twice a month, three times per month, or more. In some embodiments, the liposomal compositions described herein are administered twice daily administration, e.g., morning and evening. In some embodiments, the liposomal compositions described herein are administered for at least 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 12 months, 18 months, 2 years, 3 years, 4 years, 5 years, 10 years, or more.

Liposomal compositions as described herein may be administered prior to a non-invasive fat reduction procedure or an invasive fat reduction procedure. In some instances, the liposomal compositions described herein are administered up to 1 day, up to 2 days, up to 3 days, up to 5 days, up to 7 days, up to 14 days, up to 21 days, or more than 21 days prior to a fat reduction procedure. Sometimes the liposomal compositions described herein are administered singly, or over a time course, such as daily, multiple times weekly, weekly, biweekly, monthly or less frequently prior to a fat reduction procedure. In some instances, the liposomal compositions described herein are administered singly, or over a time course, such as daily, multiple times weekly, weekly, biweekly, monthly or more frequently prior to a fat reduction procedure.

Liposomal compositions as described herein may be administered during a non-invasive fat reduction procedure or an invasive fat reduction procedure.

Liposomal compositions as described herein may be administered following a non-invasive fat reduction procedure or an invasive fat reduction procedure. In some instances, the liposomal compositions described herein are administered up to 1 day, up to 2 days, up to 3 days, up to 5 days, or more than 5 days following a fat reduction procedure. Sometimes the liposomal compositions described herein are administered singly, or over a time course, such as daily, multiple times weekly, weekly, biweekly, monthly or less frequently following a fat reduction procedure. In some instances, the liposomal compositions described herein are administered singly, or over a time course, such as daily, multiple times weekly, weekly, biweekly, monthly or more frequently following a fat reduction procedure. In some instances, the liposomal compositions described herein are administered in combination with a second composition. In some instances, the second composition is administered before the liposomal compositions described herein. In some instances, the second composition is administered after the liposomal compositions described herein. In some instances, the second composition is administered together with the liposomal compositions described herein. In some instances, the second composition is administered prior to the fat reduction procedure. In some instances, the second composition is administered after the fat reduction procedure. In some instances, the second composition comprises a liposome. In some instances, the second composition comprises a liposome encapsulating a peptide.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Preparation of Liposomal Compositions

Figure 1B:
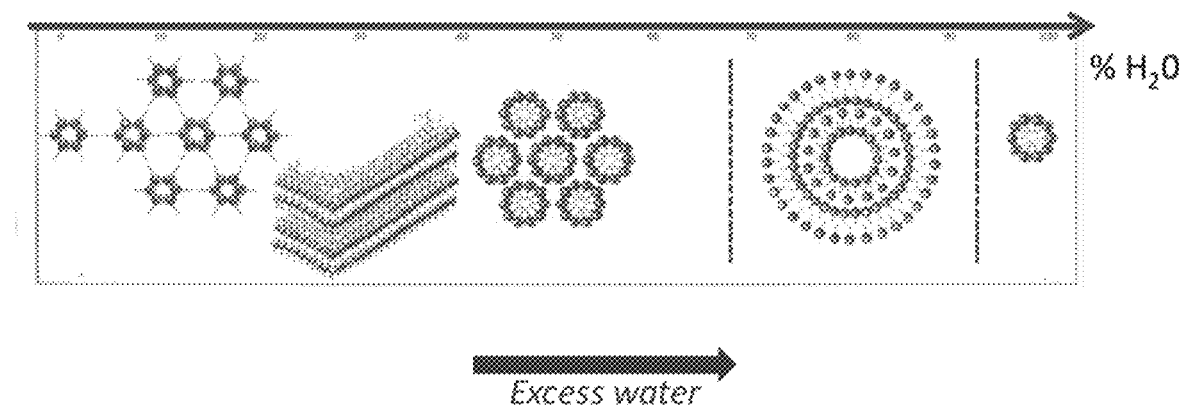
Figure 2:
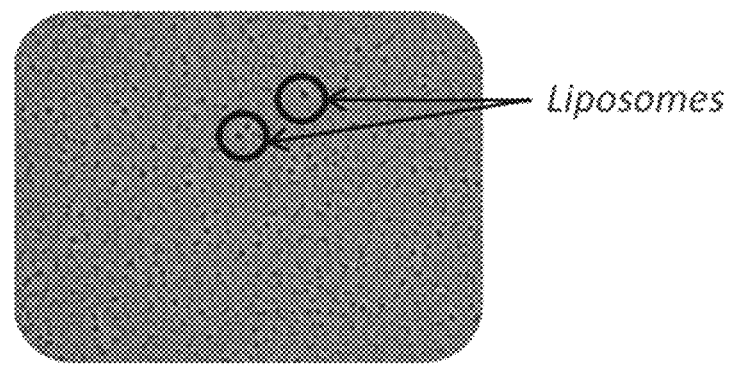
FIG. 2 shows an image of a liposome.

A liposomal preparation was prepared according to the schematic as seen in FIG. 1A. FIG. 1A shows the various methods for creating liposomes including hydrosoluble ingredient entrapment, liposoluble ingredient entrapment, and a liposoluble and hydrosoluble ingredient entrapment. FIG. 1B shows a schematic of liposomal formation. Liposomes were observed following the liposome suspension process manufacturing as seen in FIG. 2.

Example 2: Efficacy of Liposomal Compositions

Efficacy of liposomal compositions was tested for bioavailability and skin penetration.

A water suspension of liposomes was prepared with 1.5% of hydrophilic molecule A or 300 ppm (0.03%) hydrophilic molecule B, and 27% Pro-Lipo™ Neo. Molecule A was caffeine and had a molecular weight of 194.2 g/mol and a penetration ability of log Kow of −0.07. Molecule B was a hexapeptide (hexapeptide-38) with a molecular weight of (870 g/mol) and a penetration ability log Kow of −1.13. A water solution with 1.5% A or 300 ppm B was used as a control (non-entrapped molecule).

A dose of 10 mg/cm² was applied on skin explants using the Franz cell method. The kinetic of the molecules passed through skin explants was measured during 24 hours. After 24 hours, the molecule content was measured in each skin compartment including the stratum corneum, epidermis, dermis, and receptor fluid.

Figure 3A:
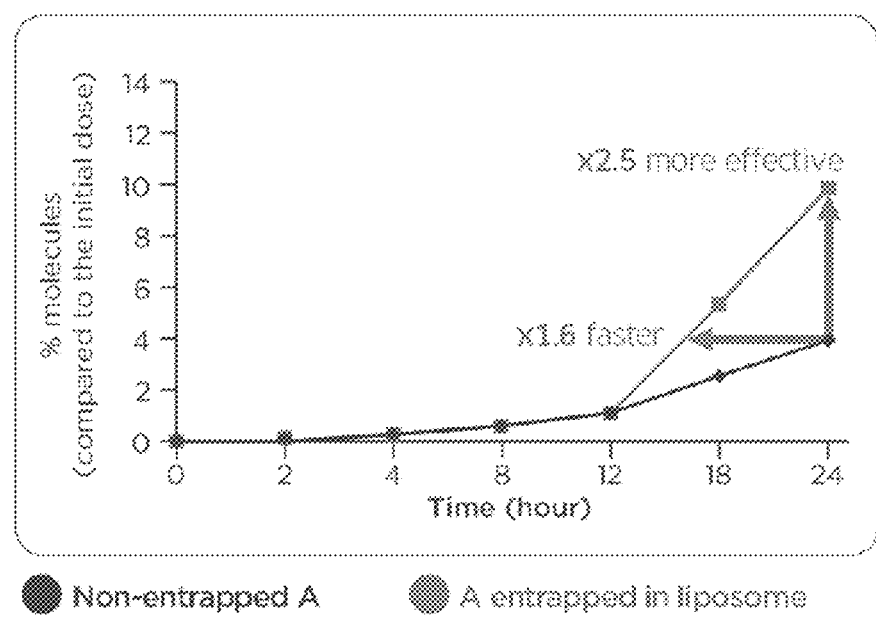
FIG. 3A shows a graph of diffusion of Molecule A through human skin.
Figure 3B:
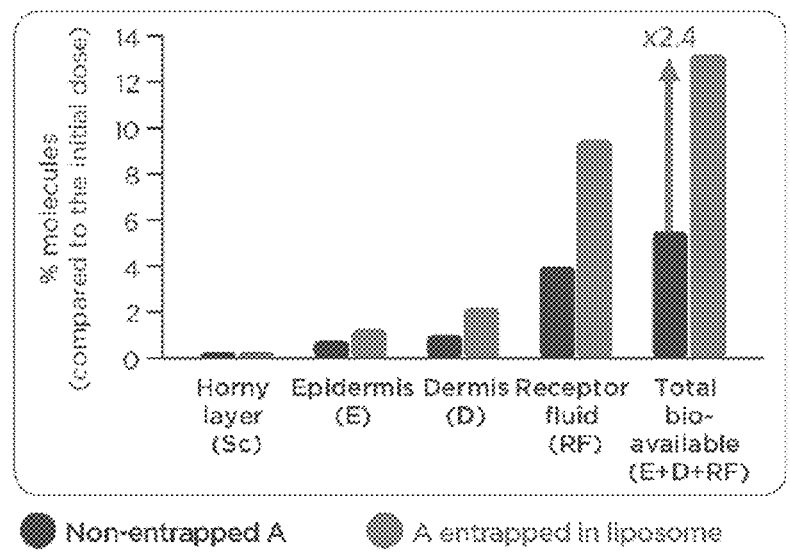
FIG. 3B shows a graph of skin distribution of Molecule A.
Figure 3C:
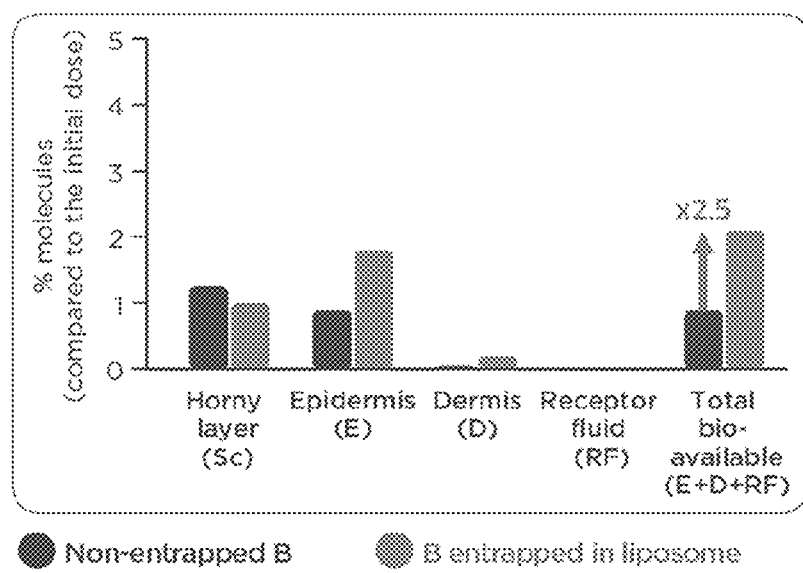
FIG. 3C shows a graph of skin distribution of Molecule B after 24 hours.

FIGS. 3A-3B show graphs of diffusion of Molecule A through the human skin (FIG. 3A) and skin distribution of Molecule A (FIG. 3B). As seen in FIG. 3A, Molecule A formulated in liposomes was 2.5× more effective and 1.6× faster than non-entrapped molecule. As seen in FIG. 3B, Molecule A formulated in liposomes was 2.4× more efficacious at total bioavailability after 24 hours. Molecule B formulated in liposomes also exhibited increased bioavailability as seen as a 2.5× increase in skin distribution of Molecule B after 24 hours (FIG. 3C).

Example 3: Particle Size of Liposomal Acetyl Hexapeptide 38

The particle size of liposomal acetyl hexapeptide 38 was determined.

100 uL of liposomal acetyl hexapeptide 38 was dissolved in 15 mL of water. Assay information can be seen in Table 1 for two experiments.

TABLE 1

|  | Experiment 1 | Experiment 2 |
| --- | --- | --- |
| Material RI | 1.59 | 1.59 |
| Material Absorption | 0.010 | 0.010 |
| Dispersant Name | Water | Water |
| Dispersant RI | 1.330 | 1.330 |
| Viscosity (cP) | 0.8872 | 0.8872 |
| Temperature (° C.) | 25 | 25 |
| Count Rate (kcps) | 149.1 | 149.1 |
| Cell Description | Disposable sizing cuvette | Disposable sizing cuvette |
| Duration Used (s) | 80 | 80 |
| Measurement position (mm) | 4.65 | 4.65 |
| Attenuator | 7 | 7 |

Results from the experiments can be seen in Tables 2-4 and FIGS. 4A-4D.

TABLE 2

PdI refers to polydispersity index and the intercept refers to amplitude.

|  | Experiment 1 | Experiment 2 |
| --- | --- | --- |
| Z-Average (d · nm) | 184.7 | 184.7 |
| PdI | 0.168 | 0.168 |
| Intercept | 0.961 | 0.961 |

TABLE 3

|  | Experiment 1 | | | Experiment 2 | | |
| --- | --- | --- | --- | --- | --- | --- |
|  | Diam. (nm) | % Intensity | Width (nm) | Diam. (nm) | % Intensity | Width (nm) |
| Peak 1 | 211.4 | 99.4 | 88.24 | 205.5 | 98.3 | 100.4 |
| Peak 2 | 5026 | 0.6 | 594.1 | 5228 | 1.7 | 752.1 |
| Peak 3 | 0.000 | 0.0 | 0.000 | 0.000 | 0.0 | 0.000 |

TABLE 4

| | INTENSITY-WEIGHTED | | | |
| --- | --- | --- | --- | --- |
| | CUMULANT RESULTS | | NNLS RESULTS | |
| | Z-AVERAGE (nm) | PDI | PEAK OF INTEREST (nm) | PEAK WIDTH (nm) |
| Liposomal Acetyl Hexapeptide 38 | 184.7 | 0.17 | 211.4 | 88.24 |

As seen in Tables 2-4 and FIGS. 4A-4D, a liposomal acetyl hexapeptide-38 composition was generated with a particle size of 184.7 nanometers (nm).

Example 4: Liposomal Formulations

Exemplary liposomal formulations are seen in Table 5 and Table 6.

TABLE 5

| Ingredient | % by wt. |
| --- | --- |
| Hydrogenated Lecithin, C12-16 Alcohols, Palmitic Acid | 1-6% |
| Avocado extract, Shea butter, Bentonite | 0.25-2% |
| Acetyl Tetrapeptide-2 | 1-4% |
| Phytoene/Phytofluene | 0.2-1% |
| Hydroxymethoxyphenyl Decanone- | 0.5-2% |
| TriHex-Palmitoyl Tripeptide-1 | 1-6% |
| Palmitoyl Hexapeptide-12 | 0.25-4% |
| Polyholosides from flax seeds | 2.5-10% |
| Plantago lanceolata also called "Plantain" | 1-4% |
| Dill extract | 0.25-4% |
| Phosphatidylserine | 0.025-0.1% |
| Oleuropein | 0.01-0.05% |
| Hexapeptide-11 | 0.005-0.02% |
| Hydrolyzed Candida Saitoana Extract | 1-6% |
| Centella Asiatica | 0.25-4% |
| Propanediol, Lecithin | 0.25-2% |
| Euglena Gracilis Extract, Aqua, Caffeine, Glaucium Flavum Leaf Extract | 0.05-1% |

TABLE 6

| Name | % W/W |
| --- | --- |
| Water/Aqua/Eau | 70-80 |
| Disodium EDTA | 0.05-1 |
| Niacinamide | 1-4 |
| Caprylyl Glycol, Caprylhydroxamic Acid, Glycerin | 0.25-4 |
| Phenoxyethanol, Ethylhexylglycerin | 0.25-4 |
| Water, Tremella Fuciformis Sporocarp Extract, Betaine, Glycerin | 0.25-4 |
| Glycerin, Palmitoyl Tripeptide-1 | 1-6 |
| Glycerin, Palmitoyl Hexapeptide-12 | 1-6 |
| Water, Propanediol, Ornithine, Phospholipids, Glycolipids | 1-4 |
| Glycerin, Palmitoyl Dipeptide-5 Diaminobutyroyl Hydroxythreonine, Palmitoyl Dipeptide-5 Diaminohydroxybutyrate | 0.25-4 |
| Glycerin, Palmitoyl Tripeptide-5 | 0.25-4 |
| Isopropyl Palmitate, Lecithin, Water, Swertia Chirata Extract | 1-4 |
| Polyacrylate-13, Polyisobutene, Polysorbate 20 | 1-4 |
| Squalane, Dunaliella Salina Extract | 0.25-2 |
| Propanediol (Natural, ECOCERT), Water, Phytosterols, Lecithin, Olea Europaea (Olive) Fruit Oil, Squalane, Hydrolyzed Pea Protein, Butyrospermum Parkii (Shea) Butter, Ceramide NP | 1-4 |

TABLE 6-continued

| Name | % W/W |
|---|---|
| Ergothioneine, Water | 0.25-4 |
| Tocopherol | 0.05-1 |
| Propanediol, Lecithin | 0.25-4 |
| Butylene Glycol, Aqua, Acetyl Hexapeptide-38 (liposome) | 1-4 |
| Caprylyl Methicone | 0.05-1 |
| Phosphatidylserine, Phospholipids, Tocopherol, Ascorbyl Palmitate | 0.0025-1 |

Figure 4A:
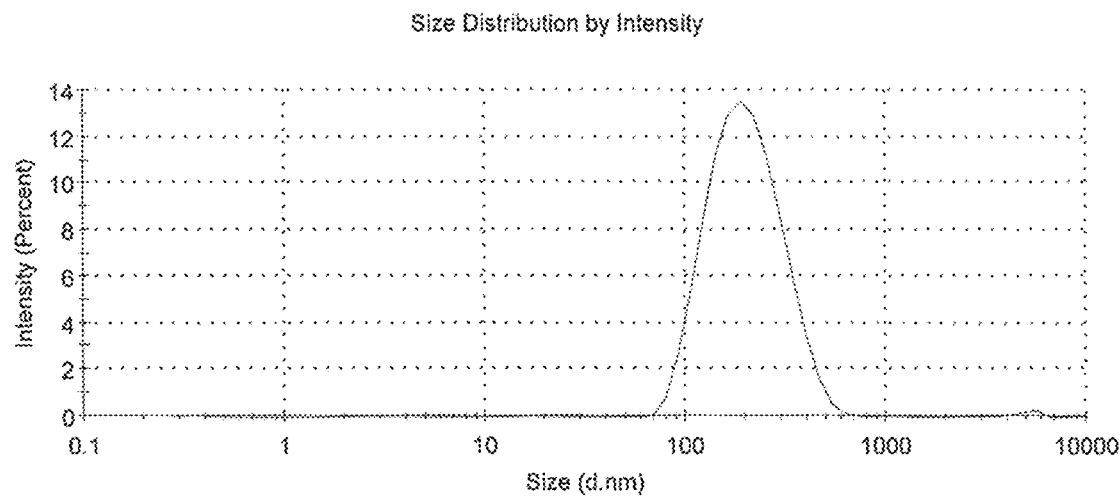
FIGS. 4A-4B show graphs of size distribution of acetyl hexapeptide-38 in a first experiment.
Figure 4B:
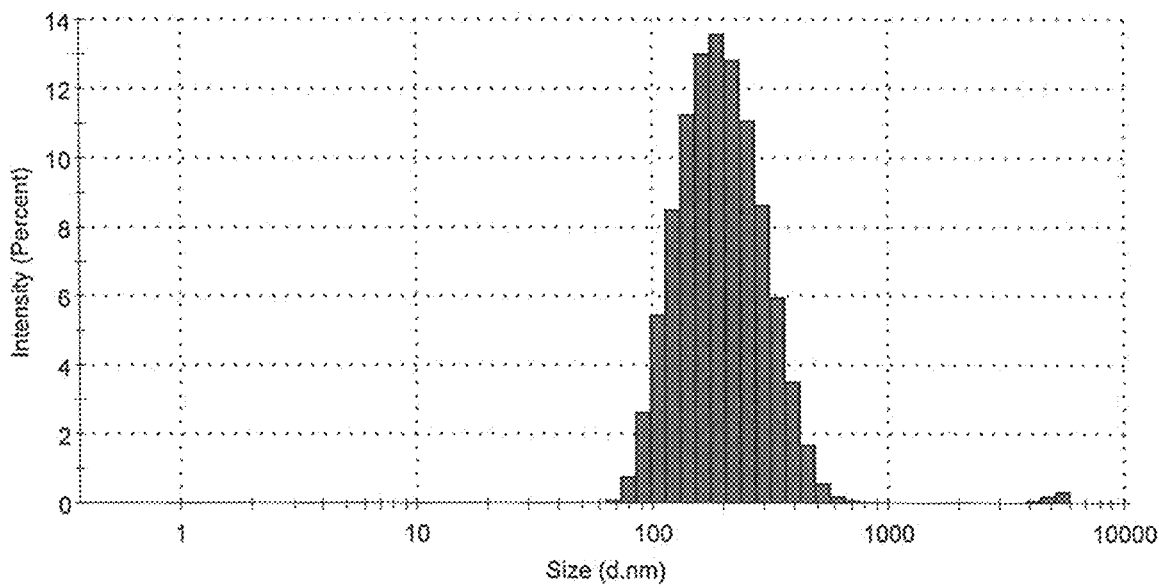
Figure 4C:
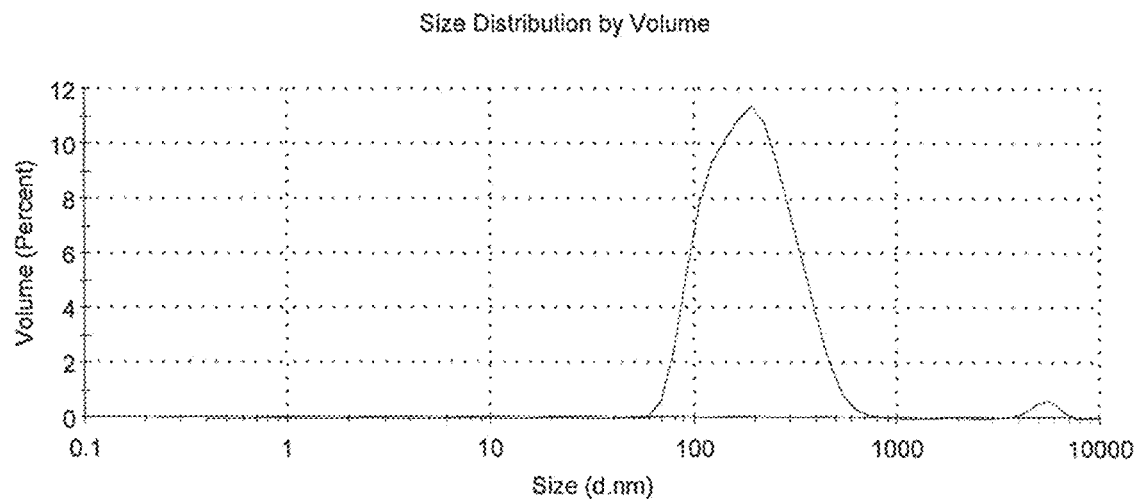
FIGS. 4C-4D show graphs of size distribution of acetyl hexapeptide-38 in a second experiment.
Figure 4D:
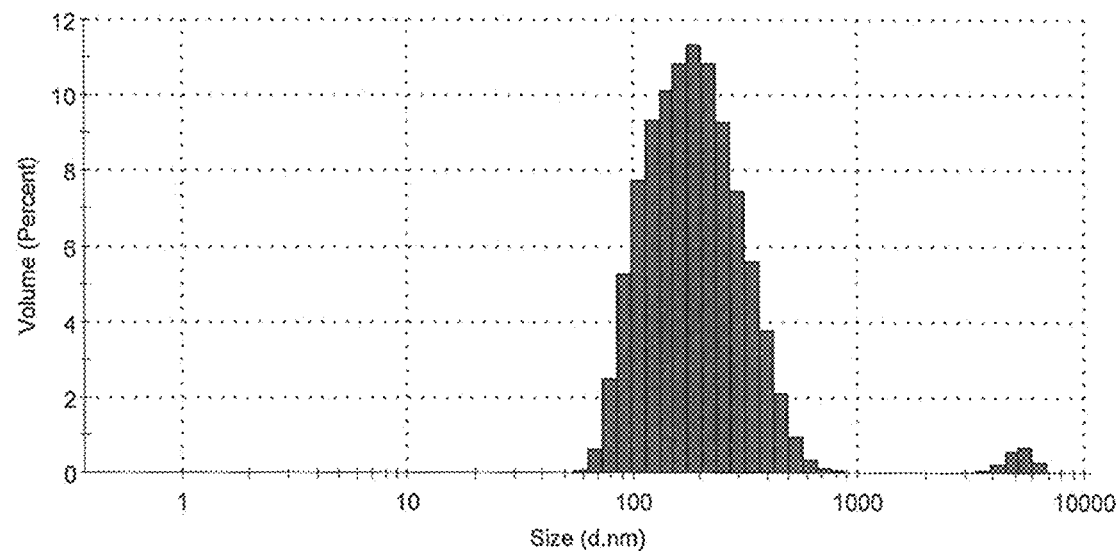
Figure 6A:
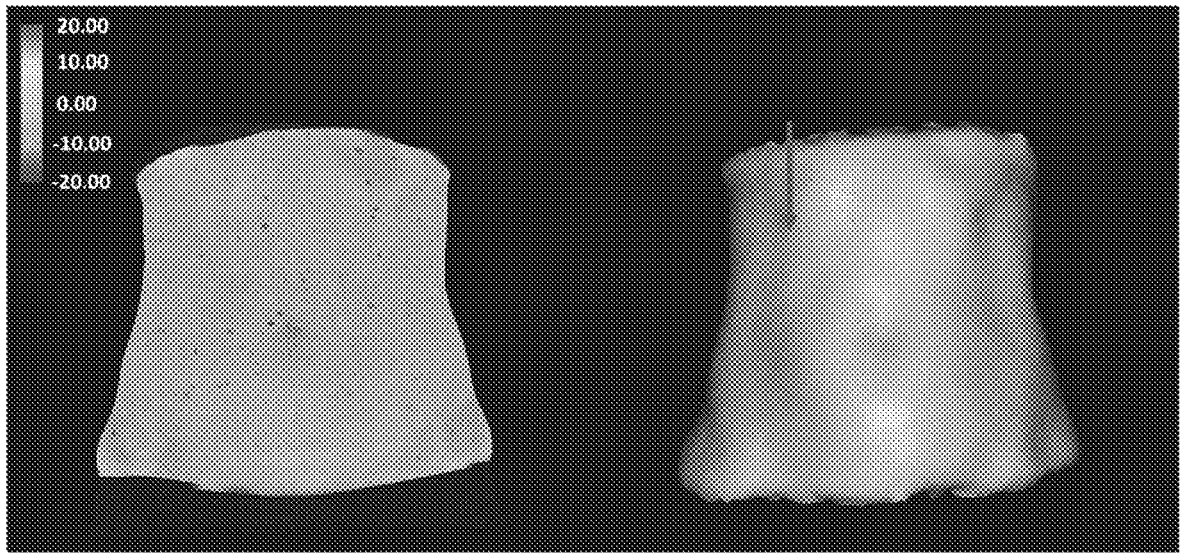
FIGS. 6A-6C show images of an abdomen of a patient treated with radiofrequency followed by regenerating body complex.
Figure 6B:
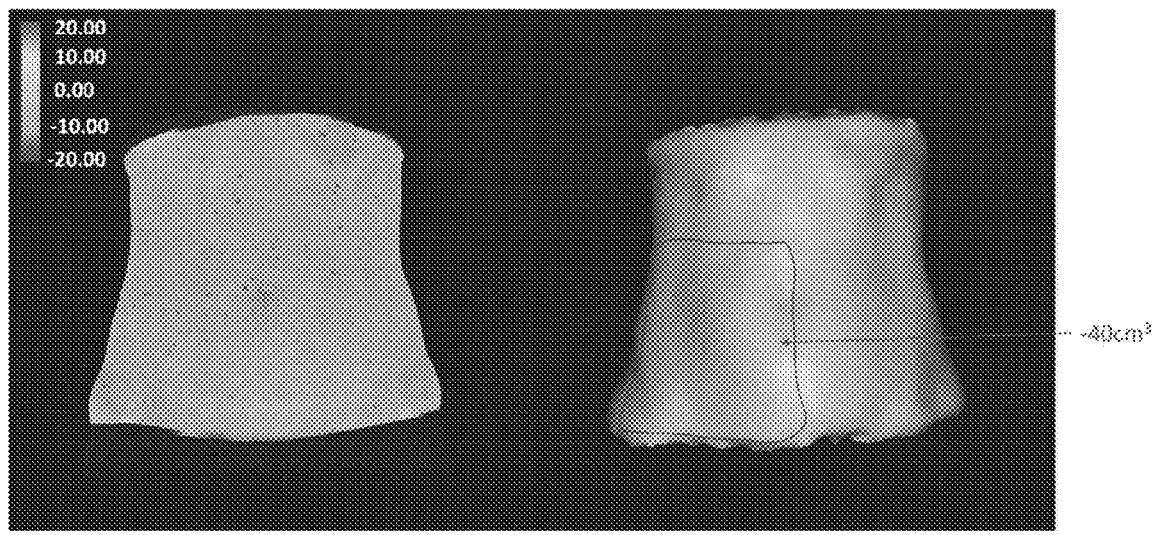
Figure 6C:
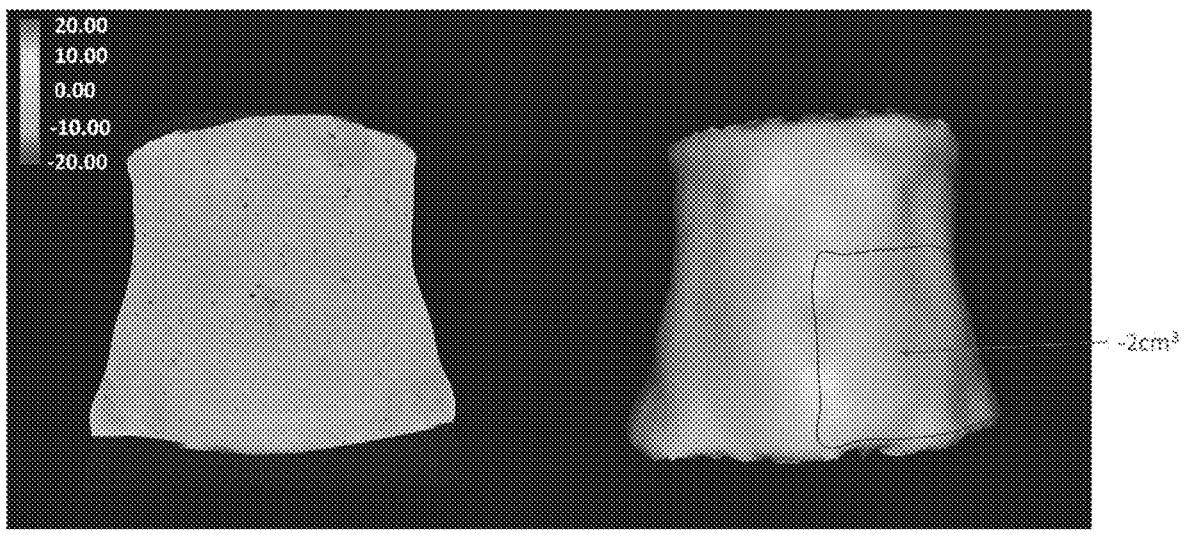

Example 5: Patient Treated with Radiofrequency Followed by Regenerating Body Complex Administration A patient underwent Vanquish ME procedure, which is a radiofrequency "hot" CoolSculpting technology. The right side of the lower abdomen below the umbilicus of the patient was administered topically regenerating body complex (Exemplary Formula 1M) following the procedure. 3D photos were taken with the QuantifiCare LifeViz® Infinity camera and software imaging system (FIGS. 6A-4C). As seen in FIGS. 6A-6C taken at week 5, 3D photos demonstrate volume and contour changes and the color scale represents volume changes in $cm^3$. The color scale is as follows: blue color represents volume reduction, red is volume increase and yellow is neutral (no change). There was a marked reduction on the right side (arrow, FIG. 6A) and further quantified as seen in FIGS. 6B-6C. There was a 40 $cm^3$ reduction as seen in FIG. 4B and a 2 $cm^3$ reduction as seen in FIG. 6C.

Figure 7A:
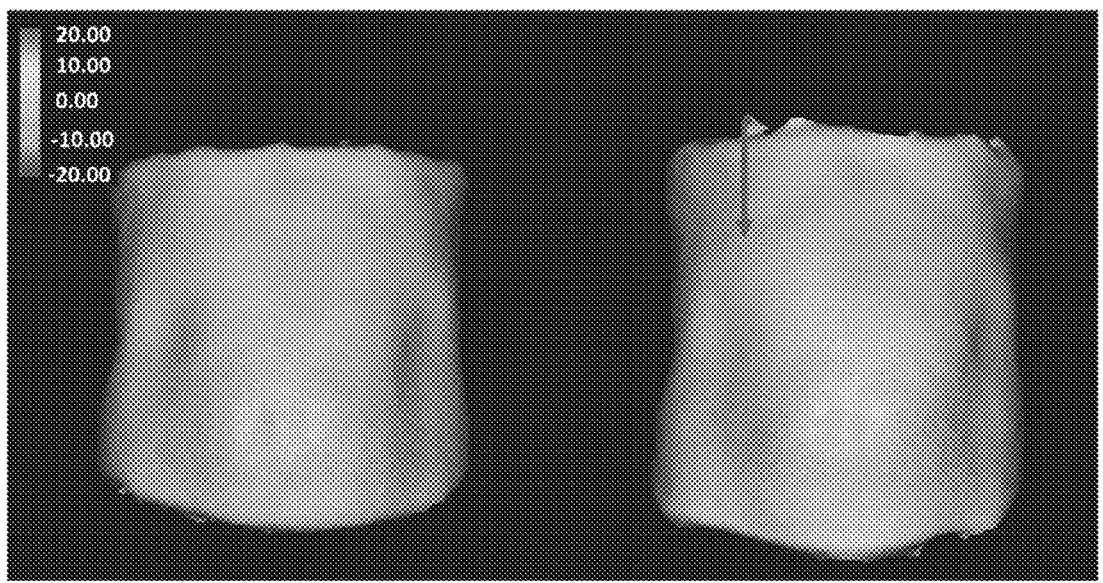
FIGS. 7A-7C show images of an abdomen of a patient treated with cryolipolysis followed by regenerating body complex.
Figure 7B:
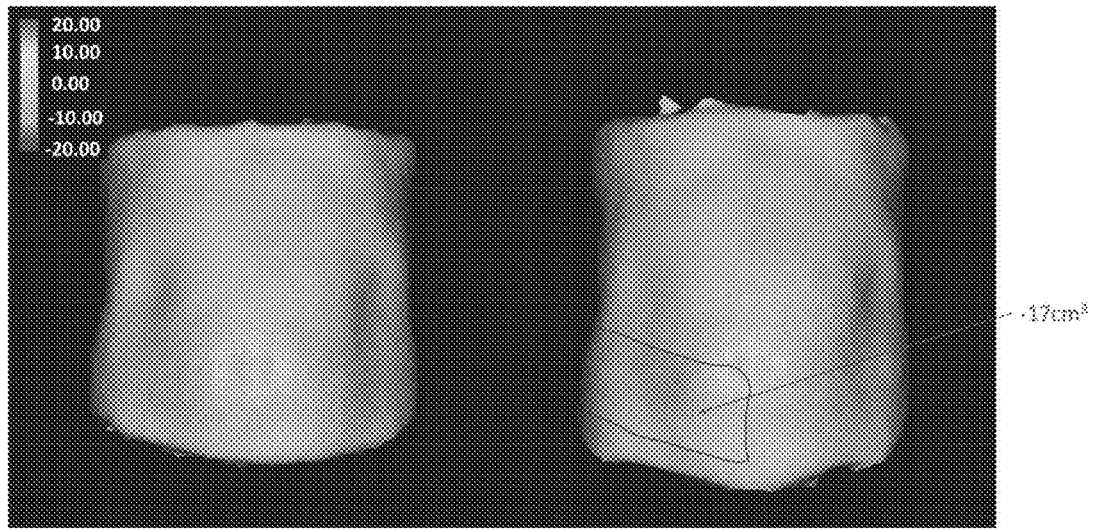
Figure 7C:
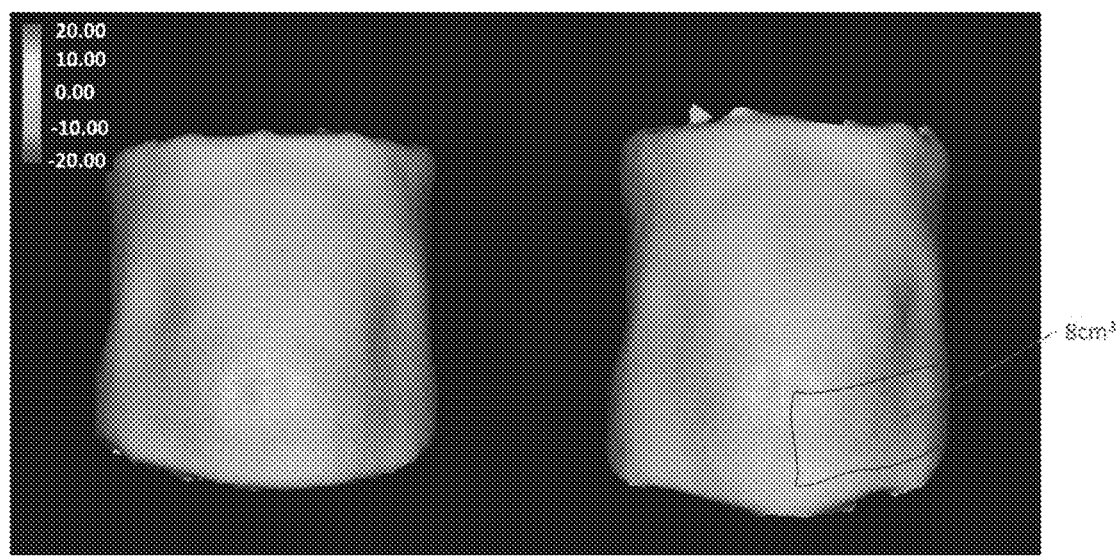

Example 6: Patient Treated with CoolSculpting Procedure Followed by Regenerating Body Complex Administration A patient underwent CoolSculpting procedure. The right side of the lower abdomen below the umbilicus of the patient was administered topically regenerating body complex (Exemplary Formula 1M) following the procedure. 3D photos were taken with the QuantifiCare LifeViz® Infinity camera and software imaging system (FIGS. 7A-7C). As seen in FIGS. 7A-7C taken at week 11, 3D photos demonstrate volume and contour changes and the color scale represents volume changes in $cm^3$. The color scale is as follows: blue color represents volume reduction, red is volume increase and yellow is neutral (no change). There was a marked reduction on the right side (arrow, FIG. 7A) and further quantified as seen in FIGS. 7B-7C. There was a 17 $cm^3$ reduction as seen in FIG. 7B and an 8 $cm^3$ change as seen in FIG. 7C.

Figure 8:
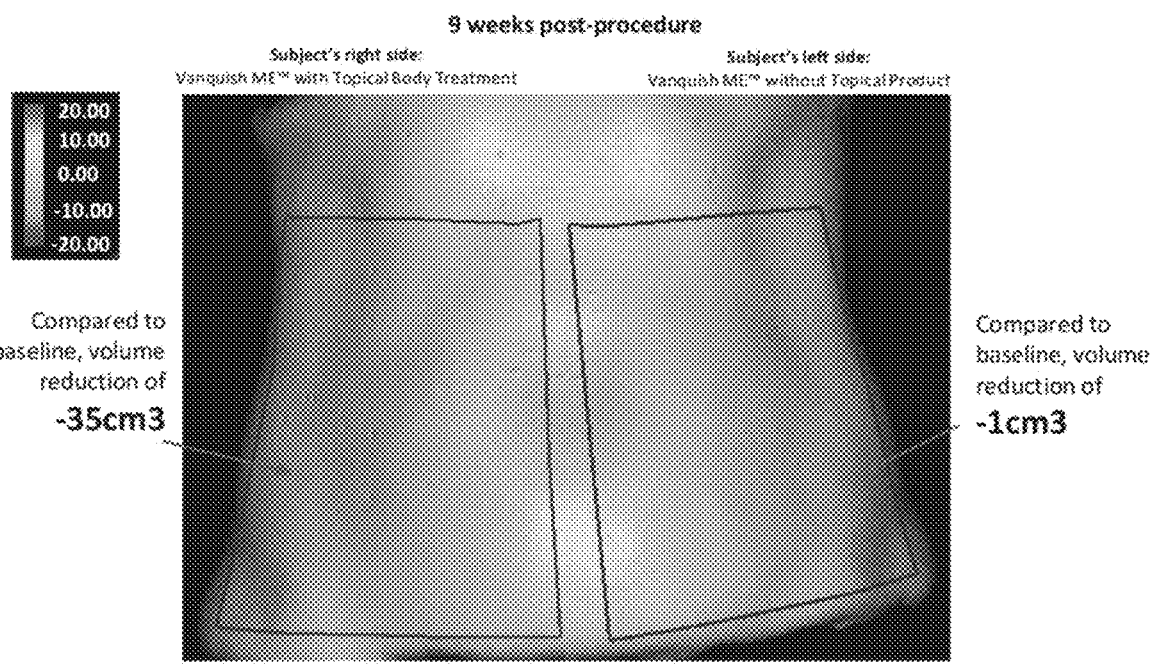
FIG. 8 shows an image of an abdomen and flanking region of a subject treated with a body sculpting device followed by regenerating body complex 9 weeks post-procedure.

Example 7: Acceleration of Fat Reduction in Patient Treated with Body Sculpting Device Followed by Regenerating Body Complex Administration A subject received a Vanquish ME™ (BTL Aesthetics) fat reduction procedure on both sides of the lower abdomen and flanks. Subject followed-up treatment with a split abdomen regimen that included the regenerating body complex (Exemplary Formula 1M) on the subject's right side and no topical treatment on the patient's left side (only the procedure treatment). Results are seen in FIG. 8. FIG. 8 shows 3D volume map results after 9 weeks post-procedure. The blue color represents volume reduction and red color represents volume increase. Treatment of the regenerating body complex on the subject's right side resulted in a volume reduction of 35 $cm^3$ as compared to the subject's left side that received no topical treatment resulting in a reduction of 1 $cm^3$ (FIG. 8).

Figure 9:
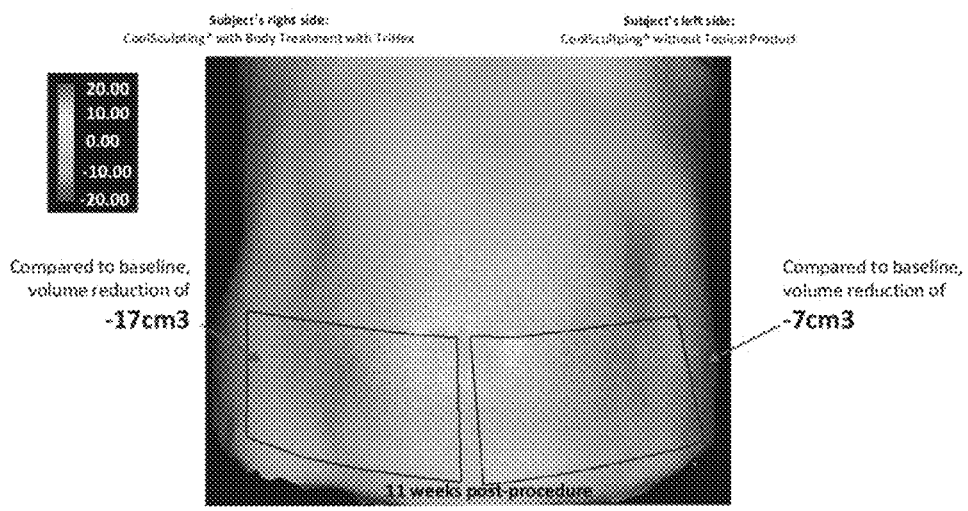
FIG. 9 shows an image of an abdomen of a subject treated with cryolipolysis followed by regenerating body complex 11 weeks post-procedure.

Example 8: Acceleration of Fat Reduction in Patient Treated with Body Sculpting Device Followed by Regenerating Body Complex Administration A subject received a CoolSculpting fat reduction procedure on both sides of the lower abdomen. Subject followed-up treatment with a split abdomen regimen that included the regenerating body complex (Exemplary Formula 1M) on the subject's right side and no topical treatment on the patient's left side (only the procedure treatment). Results are seen in FIG. 9. FIG. 9 shows a 3D volume map results after 11 weeks post-procedure. The blue color represents volume reduction and red color represents volume increase. Treatment of the regenerating body complex on the subject's right side resulted in a volume reduction of 17 $cm^3$ as compared to the subject's left side that received no topical treatment resulting in a reduction of 7 $cm^3$ (FIG. 9).

Example 9: Acceleration of Fat Reduction in Patient Treated with Body Sculpting Device Followed by Regenerating Body Complex Administration after 5 Weeks A subject received a CoolSculpting fat reduction procedure on both sides of the lower abdomen and flanks. Subject followed-up treatment with a split abdomen regimen that included the regenerating body complex (Exemplary Formula 1M) on the subject's right side and no topical treatment on the patient's left side (only the procedure treatment). The case study photos were taken with the QuantifiCareLifeViz® Infinity camera and software imaging system. 3D photos are displayed in the software's clay mode to reveal volume and contour changes. The color scale and volume map represent volume changes in $cm^3$. The blue color represents volume reduction and red color represents volume increase.

Figure 10:
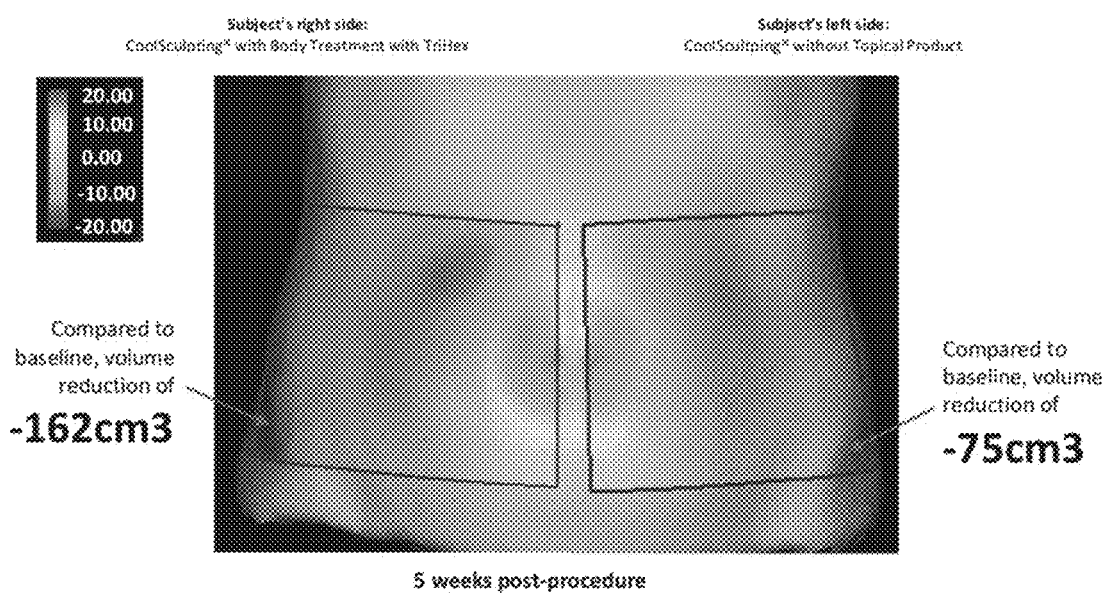
FIG. 10 shows an image of an abdomen and flanking region of a subject treated with a body sculpting device followed by regenerating body complex 5 weeks post-procedure.

Results are seen in FIG. 10. FIG. 10 shows a 3D volume map results after 5 weeks post-procedure. Treatment of the regenerating body complex on the subject's right side resulted in a volume reduction of 162 $cm^3$ as compared to the subject's left side that received no topical treatment resulting in a reduction of 75 $cm^3$ (FIG. 10).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Exemplary Embodiments

Among the exemplary embodiments are:
Embodiment 1 comprises a composition comprising a non-palmitoylated peptide encapsulated in a liposome, wherein an average particle size of the composition is no more than 220 nanometers. Embodiment 2. The composition of embodiment 1, wherein the peptide comprises an acetyl peptide. Embodiment 3. The composition of embodiment 1, wherein the peptide is a hexapeptide. Embodiment 4. The composition of embodiment 3, wherein the hexapeptide is hexapeptide-11. Embodiment 5. The composition of embodiment 3, wherein the hexapeptide is hexapeptide-38. Embodiment 6. The composition of embodiment 5, wherein the hexapeptide-38 comprises acetyl hexapeptide-38. Embodiment 7. The composition of embodiment 1, wherein the average particle size is about 150 nanometers to about 220 nanometers. Embodiment 8. The composition of embodiment 1, wherein the average particle size is about 180 nanometers to about 220 nanometers. Embodiment 9. The composition of embodiment 1, wherein the average particle size is about 185 nanometers. Embodiment 10. The composition of embodiment 1, wherein the average particle size is about 180 nanometers. Embodiment 11. The composition of embodiment 1, wherein a polydispersity index is about 0.17. Embodiment 12. The composition of embodiment 1, wherein the composition comprises about 0.03% of the peptide. Embodiment 13. The composition of embodiment 1, wherein the composition comprises about 0.01% to about 5% of the peptide. Embodiment 14. The composition of embodiment 1, wherein the composition comprises at most about 5% of the peptide. Embodiment 15. The composition of embodiment 1, wherein the composition comprises about 27% of liposomes. Embodiment 16. The composition of embodiment 1, wherein the composition comprises about 20% to about 40% of liposomes. Embodiment 17. The composition of embodiment 1, wherein the composition comprises about 10% to about 30% of liposomes. Embodiment 18. The composition of embodiment 1, wherein the composition is oil free. Embodiment 19. The composition of embodiment 1, wherein the composition is preservative free. Embodiment 20. The composition of embodiment 1, wherein the composition comprises a pH in a range of about 5 to about 8. Embodiment 21. The composition of embodiment 1, wherein the composition comprises about 1.5×, 2.0×, 2.5×, 3.0×, or 4.0× improved efficacy as compared to a composition not comprising liposomes. Embodiment 22. The composition of embodiment 1, wherein the composition comprises about 1.5×, 2.0×, 2.5×, 3.0×, or 4.0× improved distribution as compared to a composition not comprising liposomes. Embodiment 23. The composition of embodiment 1, wherein the composition comprises about 1.5×, 2.0×, 2.5×, 3.0×, or 4.0× increased activity as compared to a composition not comprising liposomes. Embodiment 24. The composition of embodiment 1, wherein the composition is a topical composition. Embodiment 25. The composition of embodiment 4, further comprising hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof. Embodiment 26. The composition of embodiment 25, further comprising a tripeptide, a tetrapeptide, and a second hexapeptide. Embodiment 27. The composition of embodiment 26, wherein the tripeptide is tripeptide-1. Embodiment 28. The composition of embodiment 27, wherein the tripeptide-1 comprises palmitoyl tripeptide-1, myristoyl tripeptide-1, or a combination thereof. Embodiment 29. The composition of embodiment 26, wherein the tetrapeptide is tetrapeptide-2. Embodiment 30. The composition of embodiment 29, wherein the tetrapeptide-2 comprises acetyl tetrapeptide-2. Embodiment 31. The composition of embodiment 26, wherein the second hexapeptide is hexapeptide-12. Embodiment 32. The composition of embodiment 31, wherein the hexapeptide-12 comprises palmitoyl hexapeptide-12, myristoyl hexapeptide-12, or a combination thereof. Embodiment 33. The composition of embodiment 6, further comprising a tripeptide, a dipeptide, and a second hexapeptide. Embodiment 34. The composition of embodiment 33, wherein the tripeptide is tripeptide-1. Embodiment 35. The composition of embodiment 34, wherein the tripeptide-1 comprises palmitoyl tripeptide-1, myristoyl tripeptide-1, or a combination thereof. Embodiment 36. The composition of embodiment 33, wherein the tripeptide is tripeptide-5. Embodiment 37. The composition of embodiment 36, wherein the tripeptide-5 comprises palmitoyl tripeptide-5, myristoyl tripeptide-5, or a combination thereof. Embodiment 38. The composition of embodiment 33, wherein the second hexapeptide is hexapeptide-12. Embodiment 39. The composition of embodiment 38, wherein the hexapeptide-12 comprises palmitoyl hexapeptide-12, myristoyl hexapeptide-12, or a combination thereof. Embodiment 40. The composition of embodiment 34, wherein the dipeptide is dipeptide-5. Embodiment 41. The composition of embodiment 6, further comprising water, glycerin, propanediol, niacinamide, isopropyl palmitate, polyacrylate-13, phosphatidylserine, ascorbyl palmitate, *Swertia chirata* extract, hydrolyzed pea protein, ornithine, ceramide NP, ergothioneine, *Dunaliella salina* extract, phytosterols, phospholipids, glycolipids, *Tremella fuciformis* sporocarp extract, *Olea europaea* (olive) fruit oil, *Butyrospermum parkii* (shea) butter, betaine, squalane, lecithin, caprylyl methicone, disodium EDTA, polysorbate 20, tocopherol, butylene glycol, caprylyl glycol, caprylhydroxamic acid, polyisobutene, ethylhexylglycerin, phenoxyethanol, or combinations thereof.

Embodiment 42. The composition of embodiment 1, wherein the liposome comprises phospholipids. Embodiment 43. The composition of embodiment 1, wherein the liposome comprises phospholipids, fatty acids, or fatty acid groups. Embodiment 44. The composition of embodiment 42 or 43, wherein the phospholipids are unsaturated. Embodiment 45. The composition of embodiment 42 or 43, wherein the phospholipids have a transition phase temperature from about 10° C. to about 25° C. Embodiment 46. A composition comprising a peptide encapsulated in a liposome, wherein an average particle size of the composition is no more than 220 nanometers, and wherein the peptide is not functionalized or is functionalized with a functional group comprising no more than fourteen carbons. Embodiment 47. The composition of embodiment 46, wherein the peptide comprises an acetyl peptide. Embodiment 48. The composition of embodiment 46, wherein the peptide is a hexapeptide. Embodiment 49. The composition of embodiment 48, wherein the hexapeptide is hexapeptide-11. Embodiment 50. The composition of embodiment 48, wherein the hexapeptide is hexapeptide-38. Embodiment 51. The composition of embodiment 50, wherein the hexapeptide-38 comprises acetyl hexapeptide-38. Embodiment 52. The composition of embodiment 46, wherein the average particle size is about 150 nanometers to about 220 nanometers. Embodiment 53. The composition of embodiment 46, wherein the average particle size is about 180 nanometers to about 220 nanometers. Embodiment 54. The composition of embodiment 46, wherein the average particle size is about 185 nanometers. Embodiment 55. The composition of embodiment 46, wherein the average particle size is about 180 nanometers. Embodiment 56. The composition of embodiment 46, wherein a polydispersity index is about 0.17. Embodiment 57. The composition of embodiment 46, wherein the composition comprises about 0.03% of the peptide. Embodiment 58. The composition of embodiment 46, wherein the composition comprises about 0.01% to about 5% of the peptide. Embodiment 59. The composition of embodiment 46, wherein the composition comprises at most about 5% of the peptide. Embodiment 60. The composition of embodiment 46, wherein the composition comprises about 27% of liposomes. Embodiment 61. The composition of embodiment 46, wherein the composition comprises about 20% to about 40% of liposomes. Embodiment 62. The composition of embodiment 46, wherein the composition comprises about 10% to about 30% of liposomes. Embodiment 63. The composition of embodiment 46, wherein the composition is oil free. Embodiment 64. The composition of embodiment 46, wherein the composition is preservative free. Embodiment 65. The composition of embodiment 46, wherein the composition comprises a pH in a range of about 5 to about 8. Embodiment 66. The composition of embodiment 46, wherein the composition comprises about 1.5×, 2.0×, 2.5×, 3.0×, or 4.0× improved efficacy as compared to a composition not comprising liposomes. Embodiment 67. The composition of embodiment 46, wherein the composition comprises about 1.5×, 2.0×, 2.5×, 3.0×, or 4.0× improved distribution as compared to a composition not comprising liposomes. Embodiment 68. The composition of embodiment 46, wherein the composition comprises about 1.5×, 2.0×, 2.5×, 3.0×, or 4.0× increased activity as compared to a composition not comprising liposomes. Embodiment 69. The composition of embodiment 46, wherein the composition is a topical composition. Embodiment 70. The composition of embodiment 49, further comprising hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof. Embodiment 71. The composition of embodiment 70, further comprising a tripeptide, a tetrapeptide, and a second hexapeptide. Embodiment 72. The composition of embodiment 71, wherein the tripeptide is tripeptide-1. Embodiment 73. The composition of embodiment 72, wherein the tripeptide-1 comprises palmitoyl tripeptide-1, myristoyl tripeptide-1, or a combination thereof. Embodiment 74. The composition of embodiment 71, wherein the tetrapeptide is tetrapeptide-2. Embodiment 75. The composition of embodiment 74, wherein the tetrapeptide-2 comprises acetyl tetrapeptide-2. Embodiment 76. The composition of embodiment 71, wherein the second hexapeptide is hexapeptide-12. Embodiment 77. The composition of embodiment 76, wherein the hexapeptide-12 comprises palmitoyl hexapeptide-12, myristoyl hexapeptide-12, or a combination thereof. Embodiment 78. The composition of embodiment 51, further comprising a tripeptide, a dipeptide, and a second hexapeptide. Embodiment 79. The composition of embodiment 78, wherein the tripeptide is tripeptide-1. Embodiment 80. The composition of embodiment 79, wherein the tripeptide-1 comprises palmitoyl tripeptide-1, myristoyl tripeptide-1, or a combination thereof. Embodiment 81. The composition of embodiment 78, wherein the tripeptide is tripeptide-5. Embodiment 82. The composition of embodiment 81, wherein the tripeptide-5 comprises palmitoyl tripeptide-5, myristoyl tripeptide-5, or a combination thereof. Embodiment 83. The composition of embodiment 78, wherein the second hexapeptide is hexapeptide-12. Embodiment 84. The composition of embodiment 83, wherein the hexapeptide-12 comprises palmitoyl hexapeptide-12, myristoyl hexapeptide-12, or a combination thereof. Embodiment 85. The composition of embodiment 78, wherein the dipeptide is dipeptide-5. Embodiment 86. The composition of embodiment 46, wherein the liposome comprises phospholipids. Embodiment 87. The composition of embodiment 46, wherein the liposome comprises phospholipids, fatty acids, or fatty acid groups. Embodiment 88. The composition of embodiment 86 or 87, wherein the phospholipids are unsaturated. Embodiment 89. The composition of embodiment 86 or 87, wherein the phospholipids have a transition phase temperature from about 10° C. to about 25° C. Embodiment 90. The composition of embodiment 51, further comprising water, glycerin, propanediol, niacinamide, isopropyl palmitate, polyacrylate-13, phosphatidylserine, ascorbyl palmitate, *Swertia chirata* extract, hydrolyzed pea protein, ornithine, ceramide NP, ergothioneine, *Dunaliella salina* extract, phytosterols, phospholipids, glycolipids, *Tremella fuciformis* sporocarp extract, *Olea europaea* (olive) fruit oil, *Butyrospermum parkii* (shea) butter, betaine, squalane, lecithin, caprylyl methicone, disodium EDTA, polysorbate 20, tocopherol, butylene glycol, caprylyl glycol, caprylhydroxamic acid, polyisobutene, ethylhexylglycerin, phenoxyethanol, or combinations thereof.

Embodiment 91. A method for preparing a composition comprising a peptide encapsulated in a liposome, comprising: a. combining the peptide and a solvent to form a mixture; and b. contacting the mixture with an aqueous solution comprising liposomes; wherein an average particle size of the composition is no more than 220 nanometers. Embodiment 92. The method of embodiment 91, wherein the contacting occurs at a temperature between about 10° C. to about 25° C. Embodiment 93. The method of embodiment 91, wherein the contacting occurs at a temperature between about 21° C. to about 25° C. Embodiment 94. The method of embodiment 91, wherein the peptide comprises an acetyl peptide. Embodiment 95. The method of embodiment 91, wherein the peptide is a hexapeptide. Embodiment 96. The method of embodiment 95, wherein the hexapeptide is hexapeptide-11. Embodiment 97. The method of embodiment 95, wherein the hexapeptide is hexapeptide-38. Embodiment 98. The method of embodiment 97, wherein the hexapeptide-38 comprises acetyl hexapeptide-38. Embodiment 99. The method of embodiment 91, wherein the solvent is butylene glycol. Embodiment 100. The method of embodiment 91, wherein the solvent is propanediol. Embodiment 101. The method of embodiment 91, wherein the solvent is water. Embodiment 102. The method of embodiment 91, wherein the average particle size is about 150 nanometers to about 220 nanometers. Embodiment 103. The method of embodiment 91, wherein the average particle size is about 180 nanometers to about 220 nanometers. Embodiment 104. The method of embodiment 91, wherein the average particle size is about 185 nanometers. Embodiment 105. The method of embodiment 91, wherein the average particle size is about 180 nanometers. Embodiment 106. The method of embodiment 91, wherein a polydispersity index is about 0.17. Embodiment 107. The method of embodiment 91, wherein the composition comprises about 0.03% of the peptide. Embodiment 108. The method of embodiment 91, wherein the composition comprises about 0.01% to about 5% of the peptide. Embodiment 109. The method of embodiment 91, wherein the composition comprises at most about 5% of the peptide. Embodiment 110. The method of embodiment 91, wherein the composition comprises about 27% of liposomes. Embodiment 111. The method of embodiment 91, wherein the composition comprises about 20% to about 40% of liposomes. Embodiment 112. The method of embodiment 91, wherein the composition comprises about 10% to about 30% of liposomes. Embodiment 113. The method of embodiment 91, wherein the composition is oil free. Embodiment 114. The method of embodiment 91, wherein the composition is preservative free. Embodiment 115. The method of embodiment 91, wherein the composition comprises a pH in a range of about 5 to about 8. Embodiment 116. The method of embodiment 91, wherein the composition comprises about 1.5×, 2.0×, 2.5×, 3.0×, or 4.0× improved efficacy as compared to a composition not comprising liposomes. Embodiment 117. The method of embodiment 91, wherein the composition comprises about 1.5×, 2.0×, 2.5×, 3.0×, or 4.0× improved distribution as compared to a composition not comprising liposomes. Embodiment 118. The method of embodiment 91, wherein the composition is a topical composition. Embodiment 119. The method of embodiment 91, wherein the aqueous solution comprises about 50%, 60%, 70%, 80%, or 90% water. Embodiment 120. The method of embodiment 91, wherein the aqueous solution comprises a ratio of about 1:9 to about 3:7 liposomes to water. Embodiment 121. The method of embodiment 91, wherein the liposome comprises phospholipids. Embodiment 122. The method of embodiment 91, wherein the liposome comprises phospholipids, fatty acids, or fatty acid groups. Embodiment 123. The method of embodiment 121 or 122, wherein the phospholipids are unsaturated. Embodiment 124. The method of embodiment 121 or 122, wherein the phospholipids have a transition phase temperature from about 10° C. to about 25° C. Embodiment 125. The method of embodiment 91, wherein an average entrapment efficacy is no more than 100%.

Embodiment 126. A method for targeting dermal white adipose tissue (dWAT) comprising: administering a composition through a hair follicle, wherein the composition penetrates the hair follicle to the dWAT. Embodiment 127. The method of embodiment 126, wherein the composition comprises a peptide encapsulated in a liposome. Embodiment 128. The method of embodiment 127, wherein the peptide is a hexapeptide. Embodiment 129. The method of embodiment 128, wherein the hexapeptide is hexapeptide-11. Embodiment 130. The method of embodiment 127, wherein an average particle size of the composition is no more than 220 nanometers. Embodiment 131. The method of embodiment 127, wherein an average particle size of the composition is about 150 nanometers to about 220 nanometers. Embodiment 132. The method of embodiment 127, wherein an average particle size of the composition is about 180 nanometers to about 220 nanometers. Embodiment 133. The method of embodiment 127, wherein an average particle size of the composition is about 185 nanometers. Embodiment 134. The method of embodiment 127, wherein an average particle size of the composition is about 180 nanometers. Embodiment 135. The method of embodiment 127, wherein an active ingredient of the composition is no more than about 600 Daltons. Embodiment 136. The method of embodiment 127, wherein an active ingredient of the composition is no more than about 700, 800, 900, or 1000 Daltons. Embodiment 137. The method of embodiment 127, wherein the composition comprises about 1.5×, 2.0×, 2.5×, 3.0×, or 4.0× improved efficacy as compared to a composition not comprising liposomes. Embodiment 138. The method of embodiment 127, wherein the composition comprises about 1.5×, 2.0×, 2.5×, 3.0×, or 4.0× improved distribution as compared to a composition not comprising liposomes. Embodiment 139. The method of embodiment 127, wherein the composition comprises about 1.5×, 2.0×, 2.5×, 3.0×, or 4.0× increased activity as compared to a composition not comprising liposomes. Embodiment 140. The method of embodiment 127, wherein the composition is administered following a non-invasive fat reduction procedure. Embodiment 141. The method of embodiment 127, wherein the composition is administered during a non-invasive fat reduction procedure. Embodiment 142. The method of embodiment 127, wherein the composition is administered prior to a non-invasive fat reduction procedure. Embodiment 143. The method of any one of embodiments 140-142, wherein the non-invasive fat reduction procedure comprises high frequency focused ultrasound, pulsed focus ultrasound, cryolipolysis, radiofrequency induced electroporation, injectable lipolytic agents, or combinations thereof. Embodiment 144. The method of embodiment 129, further comprising hydrogenated lecithin, C12-16 alcohols, palmitic acid, avocado extract, shea butter, bentonite, phytoene/phytofluene, hydroxymethoxyphenyl decanone, polyholosides, *Plantago lanceolata*, dill extract, phosphatidylserine, oleuropein, hydrolyzed *Candida saitoana* extract, *Centella asiatica*, propanediol, lecithin, *Euglena gracilis* extract, aqua, caffeine, *Glaucium flavum* leaf extract, or combinations thereof. Embodiment 145. The method of embodiment 144, further comprising a tripeptide, a tetrapeptide, and a second hexapeptide. Embodiment 146. The method of embodiment 144, wherein the tripeptide is tripeptide-1. Embodiment 147. The method of embodiment 146, wherein the tripeptide-1 comprises palmitoyl tripeptide-1, myristoyl tripeptide-1, or a combination thereof. Embodiment 148. The method of embodiment 144, wherein the tetrapeptide is tetrapeptide-2. Embodiment 149. The method of embodiment 148, wherein the tetrapeptide-2 comprises acetyl tetrapeptide-2. Embodiment 150. The method of embodiment 144, wherein the second hexapeptide is hexapeptide-12. Embodiment 151. The method of embodiment 150, wherein the hexapeptide-12 comprises palmitoyl hexapeptide-12, myristoyl hexapeptide-12, or a combination thereof.

What we claim is:

1. A topical composition comprising:
   a non-palmitoylated hexapeptide-11 encapsulated in a liposome, wherein an average particle size of the liposome is no more than 220 nanometers, wherein the hexapeptide-11 is present at a concentration of 0.001 wt. % to 0.05 wt. %, relative to the total weight of the topical composition;
   a tripeptide-1;
   a hexapeptide-12; and
   a tetrapeptide-2.

2. The composition of claim 1, wherein the non-palmitoylated hexapeptide-11 is not functionalized or is functionalized with a functional group comprising no more than fourteen carbons.

3. The composition of claim 1, wherein the average particle size is about 150 nanometers to about 220 nanometers.

4. The composition of claim 1, wherein the average particle size is about 180 nanometers to about 220 nanometers.

5. The composition of claim 1, further comprising -a a dipeptide.

6. The composition of claim 1, wherein the tripeptide-1 comprises palmitoyl tripeptide-1, myristoyl tripeptide-1, or a combination thereof.

7. The composition of claim 1, further comprising phosphatidylserine.

8. The composition of claim 1, wherein the hexapeptide-12 comprises palmitoyl hexapeptide-12, myristoyl hexapeptide-12, or a combination thereof.

9. The composition of claim 7, wherein the phosphatidylserine is present at a concentration of 0.025 wt. % to 0.1 wt. %, relative to the total weight of the composition.

10. The composition of claim 1, further comprising water, glycerin, propanediol, niacinamide, isopropyl palmitate, polyacrylate-13, phosphatidylserine, ascorbyl palmitate, Swertia chirata extract, hydrolyzed pea protein, ornithine, ceramide NP, ergothioneine, Dunaliella salina extract, phytosterols, phospholipids, glycolipids, Tremella fuciformis sporocarp extract, *Olea europaea* fruit oil, *Butyrospermum parkii* butter, betaine, squalane, lecithin, caprylyl methicone, disodium EDTA, polysorbate 20, tocopherol, butylene glycol, caprylyl glycol, caprylhydroxamic acid, polyisobutene, ethylhexylglycerin, phenoxyethanol, or combinations thereof.

11. The composition of claim 1, wherein the hexapeptide-11 is not functionalized.

12. The composition of claim 1, wherein the hexapeptide-11 is present at a concentration of 0.005 wt. % to 0.02 wt. %, relative to the total weight of the composition.

13. The composition of claim 1, comprising the following ingredients at the following concentrations by weight, relative to the total weight of the composition:
   hydrogenated lecithin, C12-16 alcohols, and palmitic acid 1-6%
   acetyl tetrapeptide-2 1-4%
   palmitoyl tripeptide-1 1-6%
   palmitoyl hexapeptide-12 0.25-4%
   phosphatidylserine 0.025-0.1%
   hexapeptide-11 0.005-0.02%
   propanediol and lecithin 0.25-2%.

* * * * *